(12) United States Patent
Ring et al.

(10) Patent No.: US 10,829,771 B2
(45) Date of Patent: Nov. 10, 2020

(54) COMPOSITIONS AND METHODS FOR EXPRESSING POLYPEPTIDES ON THE SURFACE OF CELLS

(71) Applicant: The Board of Trustees of the Leland Stanford Junior University, Stanford, CA (US)

(72) Inventors: Aaron Michael Ring, New Haven, CT (US); Andrew Kruse, Roslindale, MA (US); Aashish Manglik, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 424 days.

(21) Appl. No.: 15/525,397

(22) PCT Filed: Nov. 9, 2015

(86) PCT No.: PCT/US2015/059787
§ 371 (c)(1),
(2) Date: May 9, 2017

(87) PCT Pub. No.: WO2016/077249
PCT Pub. Date: May 19, 2016

(65) Prior Publication Data
US 2018/0037898 A1 Feb. 8, 2018

Related U.S. Application Data

(60) Provisional application No. 62/077,756, filed on Nov. 10, 2014.

(51) Int. Cl.
*C12N 15/81* (2006.01)
*C12N 15/10* (2006.01)
(Continued)

(52) U.S. Cl.
CPC ............ *C12N 15/81* (2013.01); *C07K 14/001* (2013.01); *C07K 14/70532* (2013.01);
(Continued)

(58) Field of Classification Search
None
See application file for complete search history.

(56) References Cited

U.S. PATENT DOCUMENTS

2011/0076752 A1  3/2011  Wu et al.
2011/0086768 A1  4/2011  Turner et al.
(Continued)

FOREIGN PATENT DOCUMENTS

CN  101622274  1/2010
JP  2003235579  8/2003
(Continued)

OTHER PUBLICATIONS

Baldwin, "Analysis of Glycosylphosphatidylinositol Protein Anchors: The Prion Protein," Methods in Enzymology, Jan. 13, 2006, pp. 172-187, vol. 405, Elsevier, Amsterdam, Netherlands.
(Continued)

*Primary Examiner* — Nancy A Treptow
(74) *Attorney, Agent, or Firm* — Kyle A. Gurley; Bozicevic, Field & Franciss LLP

(57) ABSTRACT

Methods and compositions are provided for displaying a protein of interest (POI) on the surface of a eukaryotic cell by fusing the POI to a signal polypeptide, a stalk polypeptide, and a surface anchor polypeptide to generate a surface accessible fusion protein. Nucleic acids are provided that include nucleotide sequences encoding a signal polypeptide, a stalk polypeptide, and a surface anchor polypeptide. In some cases, a subject nucleic acid includes and insertion site for the insertion of a POI. In some cases, a subject nucleic acid includes a nucleotide sequence that encodes a POI. In
(Continued)

some cases a stalk polypeptide is a synthetic stalk polypeptide and various example synthetic stalk polypeptides are disclosed. In some cases, a surface anchor polypeptide is a glycosylphosphatidylinisotol (GPI) anchor domain, which can be synthetic. Kits are also provided for practicing the subject methods.

28 Claims, 3 Drawing Sheets
(3 of 3 Drawing Sheet(s) Filed in Color)

Specification includes a Sequence Listing.

(51) Int. Cl.
    *C07K 14/00*     (2006.01)
    *C07K 14/705*     (2006.01)
    *C07K 14/715*     (2006.01)
    *C07K 16/28*     (2006.01)
    *G01N 33/68*     (2006.01)

(52) U.S. Cl.
    CPC ...... C07K 14/7155 (2013.01); C07K 16/2818 (2013.01); C12N 15/1037 (2013.01); G01N 33/6854 (2013.01); G01N 33/6863 (2013.01); G01N 33/6872 (2013.01); *C07K 2317/622* (2013.01); *C07K 2319/02* (2013.01); *C07K 2319/035* (2013.01); *C07K 2319/70* (2013.01); *C07K 2319/74* (2013.01); *G01N 2333/70521* (2013.01); *G01N 2333/70532* (2013.01); *G01N 2333/7155* (2013.01)

(56) References Cited

U.S. PATENT DOCUMENTS

| | | |
|---|---|---|
| 2011/0230374 A1 | 9/2011 | Pancer et al. |
| 2012/0077252 A1* | 3/2012 | Picataggio ............ C12N 9/001 435/254.22 |
| 2012/0208769 A1 | 8/2012 | Nelson et al. |

FOREIGN PATENT DOCUMENTS

| | | |
|---|---|---|
| JP | 2010512160 | 4/2010 |
| WO | 2008072075 | 6/2008 |

OTHER PUBLICATIONS

Boder et al., "Yeast surface display for screening combinatorial polypeptide libraries", Nat Biotechnol., Jun. 1, 1997, pp. 553-557, 15(6), Nature Publishing Group, New York, NY.

Doerner et al., "Therapeutic antibody engineering by high efficiency cell screening", FEBS Letters, Jan. 21, 2014, pp. 278-287, vol. 588, Issue 2, Wiley, Hoboken, NJ.

* cited by examiner

Binding of CD47-biotin (MFI Streptavidin 647)

COMPOSITIONS AND METHODS FOR EXPRESSING POLYPEPTIDES ON THE SURFACE OF CELLS

CROSS-REFERENCE

This application is a 371 application and claims the benefit of PCT Application No. PCT/US2015/059787, filed Nov. 9, 2015, which claims benefit of U.S. Provisional Patent Application No. 62/077,756 filed Nov. 10, 2014, which application is incorporated herein by reference in its entirety.

INTRODUCTION

Expression of proteins on the surface of eukaryotic cells (e.g., yeast cells), a technique known as surface display, can be used for a diverse array of purposes. For example, because yeast are eukaryotic, using yeast for surface display is well suited for engineering and modifying mammalian proteins (e.g., via directed evolution) that require post-translational modifications for efficient folding and activity (e.g., cell-surface and secreted proteins such as antibodies, receptors, cytokines, and the like). In one example of surface display, a protein of interest is fused to the Aga2p protein, which is naturally used by yeast to mediate cell-cell contacts during mating. The current surface display methods require multiple genes to be expressed and are limited with respect to the steric accessibility of a displayed protein of interest. There is a need in the art for compositions and methods that allow for the monocistronic expression and surface display of proteins of interest, e.g., in a way that allows for an adjustable ("tunable") level of accessibility.

PUBLICATIONS

Boder, et al., *Nat Biotechnol.* 1997 Jun.; 15(6):553-7; U.S. patent application number: 20110076752

SUMMARY

Methods and compositions are provided for displaying a protein of interest (POI) on the surface of a eukaryotic cell (e.g., a mammalian cell, a fungal cell, a yeast cell, etc.) by fusing the POI to a display moiety (e.g., a moiety having a signal polypeptide, a stalk polypeptide, and a surface anchor polypeptide) to generate a surface accessible fusion protein. In some cases, a surface accessible fusion protein is introduced into a eukaryotic cell as part of a nucleic acid (e.g., a recombinant expression vector). Nucleic acids are provided that include nucleotide sequences encoding a display moiety (e.g., a moiety having a signal polypeptide, a stalk polypeptide, and a surface anchor polypeptide). In some cases, a subject nucleic acid includes an insertion site for the insertion of a POI. In some cases, a subject nucleic acid includes a nucleotide sequence that encodes a POI. In some cases a stalk polypeptide is a synthetic stalk polypeptide and various example synthetic stalk polypeptides are disclosed herein. In some cases, a surface anchor polypeptide is a glycosylphosphatidylinisotol (GPI) anchor domain. In some cases, a GPI anchor domain is a synthetic GPI anchor domain. In some cases, a surface anchor polypeptide is a transmembrane domain.

Methods are provided for measuring the binding of an agent to a POI (e.g., determining whether an agent can bind to a POI). Methods are also provided for identifying an agent that binds to a POI (e.g., screening test compounds for an agent that binds to a given POI); for identifying a polypeptide that binds to a given agent (e.g., a polypeptide that binds to agent when the agent is present at a particular concentration, e.g., to identify a polypeptide that binds to an agent with an affinity greater than or equal to a pre-determined value); and for generating a variant polypeptide that binds to an agent with an affinity that is different (e.g., greater) than the affinity of the polypeptide from which the variant was derived.

Kits are also provided that include various components of the subject compositions, and such kits can be used to practice the subject methods.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

" (FIG. 1A) Schematic of one embodiment of peptide linkage to the yeast cell surface: A protein of interest (POI) (here, the engineered SIRPa variant CV1) is secreted as a surface accessible fusion protein in which the POI is fused to (i) a signal polypeptide (which directs the protein to the secretory pathway, but which can be cleaved from the protein via post-translational processing), (ii) a stalk polypeptide (a synthetic sequence, the length of which can be modified over a wide range of lengths), (iii) a GPI anchor (e.g. a synthetic GPI anchor), and optionally (iv) an epitope tag (depicted is an HA epitope tag). (FIG. 1B) Experimental results showing the relationship between stalk length (in amino acids) and surface staining for 3 labeled probes: anti-HA antibody (~150 kD), CD47-streptavidin tetramers (~100 kD), and CD47-biotin monomers (~15 kDa). (FIG. 1C) Representative flow cytometry plots of yeast displaying CV-1 attached to different length stalks stained simultaneously with Anti-HA antibodies (Alexa488) and CD47-biotin monomers (Alexa647). The length of the tested stalk sequences, in number of amino acids, is listed above each plot.

(FIG. 2A) Schematic of peptide linkage to the yeast cell surface. The engineered SIRPA variant CV1 was secreted as a fusion to the HA epitope tag and a 649 amino-acid long synthetic stalk with a synthetic GPI anchor (i.e, CV1 was the protein of interest (POI), which was expressed as a surface accessible fusion polypeptide). The yeast strain used for these experiments was YVH10, in contrast to BJ5465 used in FIG. 1A-1C. YVH10 yeast overexpress yeast protein disulfide isomerase (PDI), enabling greater folding capacity for secreted, disulfide-bond containing proteins. (FIG. 2B) Representative flow cytometry plots of YVH10 yeast displaying CV-1 attached to a 649 amino acid stalks stained simultaneously with Anti-HA antibodies (Alexa488) and CD47-biotin monomers (Alexa647).

DETAILED DESCRIPTION

Figure 1A:
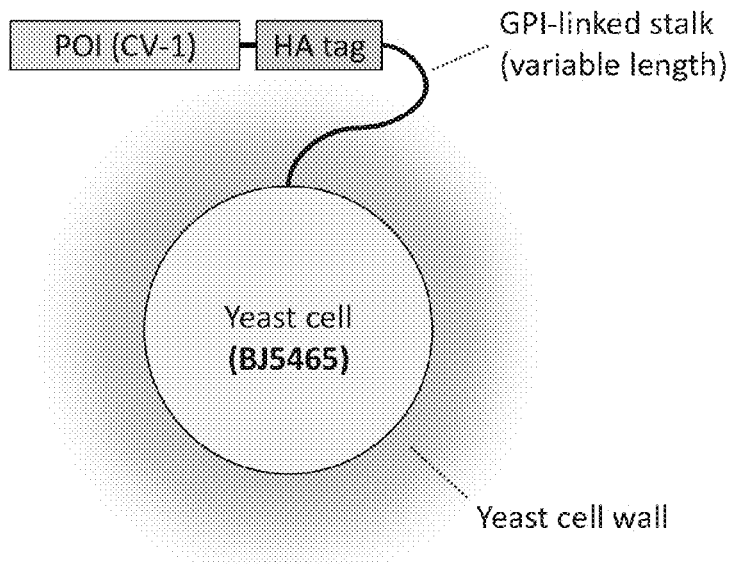
FIG. 1A-1C. Manipulation of peptide accessibility using variable-length, GPI-anchored "stalks.

Methods and compositions are provided for displaying a protein of interest (POI) on the surface of a eukaryotic cell (e.g., a mammalian cell, a fungal cell, a yeast cell, etc.) by fusing the POI to a signal polypeptide, a stalk polypeptide, and a surface anchor polypeptide to generate a surface accessible fusion protein. In some cases, a surface accessible fusion protein is introduced into a eukaryotic cell as part of a nucleic acid (e.g., a recombinant expression vector). Nucleic acids are provided that include nucleotide sequences encoding a signal polypeptide, a stalk polypeptide, and a surface anchor polypeptide. In some cases, a subject nucleic acid includes and insertion site for the insertion of a POI. In some cases, a subject nucleic acid includes a nucleotide sequence that encodes a POI. In some cases a stalk polypeptide is a synthetic stalk polypeptide and various example synthetic stalk polypeptides are disclosed herein. In some cases, a surface anchor polypeptide is a glycosylphosphatidylinisotol (GPI) anchor domain. In some cases, a GPI anchor domain is a synthetic GPI anchor domain.

Methods are provided for measuring the binding of an agent to a POI (e.g., determining whether an agent can bind to a POI). Methods are also provided for identifying an agent that binds to a POI (e.g., screening test compounds for an agent that binds to a given POI); for identifying a polypeptide that binds to a given agent (e.g., a polypeptide that binds to agent when the agent is present at a particular concentration, e.g., to identify a polypeptide that binds to an agent with an affinity greater than or equal to a pre-determined value); and for generating a variant polypeptide that binds to an agent with an affinity that is different (e.g., greater) than the affinity of the polypeptide from which the variant was derived.

Kits are also provided that include various components of the subject compositions, and such kits can be used to practice the subject methods.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "synthetic", as used when referring to components of the subject compositions (e.g., a synthetic stalk polypeptide, a synthetic surface anchor polypeptide, a synthetic signal polypeptide, and the like), means that component is non-naturally occurring. For example, a synthetic stalk polypeptide by definition comprises a non-naturally occurring amino acid sequence, a synthetic surface anchor polypeptide by definition comprises a non-naturally occurring amino acid sequence, and a synthetic signal polypeptide by definition comprises a non-naturally occurring amino acid sequence.

The term "antibody" is used in the broadest sense and specifically covers monoclonal antibodies (including full length monoclonal antibodies), polyclonal antibodies, multispecific antibodies (e.g., bispecific antibodies), and antibody fragments (e.g., Fab fragments) so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Digestion of antibodies (e.g., with enzymes such as papain, Ficin, and the like) produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and —binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety (3) single chain polypeptides containing only one heavy chain variable region, or a fragment thereof containing the three CDRs of the heavy chain variable region, without an associated light chain moiety and (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The term "label" when used herein refers to a detectable compound or composition which is conjugated directly or indirectly to a molecule. For example, an agent can be said to be "detectably labeled", or can be said to include a detectable label. The label may itself may be detectable (directly detectable label) (e.g., radioisotope labels, fluorescent labels such as fluorescent chemical adducts, etc.), or the label can be indirectly detectable, e.g., in the case of an enzymatic label, the enzyme may catalyze a chemical alteration of a substrate compound or composition and the product of the reaction is detectable. One example of an indirect label is biotin, which can be detected using streptavidin. Any convenient direct or indirect label can be used in the compositions and methods described herein.

The term "recombinant" as used herein means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms. DNA sequences encoding RNA that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant nucleic acid encodes a polypeptide, the sequence of the encoded polypeptide can be naturally occurring ("wild type") or can be a variant (e.g., a mutant) of the naturally occurring sequence.

A "vector" is a replicon, such as a plasmid, phage, virus, or cosmid, to which another DNA segment, (e.g., an "insert"), may be attached so as to bring about the replication and/or expression of the attached segment in a cell. An "expression vector" is a vector having an expression cassette (e.g., having an insert that is an expression cassette). An "expression cassette" includes a DNA sequence (coding or non-coding) operably linked to a promoter. "Operably linked" refers to a juxtaposition wherein the components so described are in a relationship permitting them to function in their intended manner. For instance, a promoter is operably linked to a nucleotide sequence if the promoter affects transcription of the nucleotide sequence (e.g., expression of the nucleotide sequence). Thus the term "recombinant expression vector," or "DNA construct" are used interchangeably herein to refer to an expression vector having an insert, where the expression vector is recombinant (i.e., includes sequences that are not naturally occuring). Recombinant expression vectors are usually generated for the purpose of expressing and/or propagating the insert(s), or for the construction of other recombinant nucleotide sequences.

Compositions

The present disclosure provides compositions and methods for expressing a protein of interest (POI) on the surface of cell (i.e., surface display), by expressing the POI as a surface accessible fusion protein. The term "surface accessible fusion protein" is used herein to describe a polypeptide having a signal polypeptide, a protein of interest (POI), a stalk polypeptide, and a surface anchor polypeptide.

Signal Polypeptide

The terms "signal polypeptide" and "signal sequence" are used interchangeably herein to refer to the amino acid sequence that is present at or near the N-terminus of proteins of the secretory pathway (e.g., secreted proteins, GPI anchored proteins, etc.) that targets proteins for delivery into the lumen of the endoplasmic reticulum (ER)). As is known in the art, signal sequences are extremely variable, both in their length and in their amino acid composition. However, signal sequences tend to be approximately 15-30 amino acids long and usually include a block of 5-10 hydrophobic amino acids.

Many proteins of the secretory pathway (e.g., secreted proteins) translocate to the ER (e.g., enter the ER lumen) during translation (co-translational). However, some small secretory proteins, such as the yeast mating factor alpha (about 70 amino acids), exhibit post-translational transport into the ER lumen. Signal sequences from different proteins can function interchangeably. In some cases, a signal sequence is cleaved during processing of the protein (e.g., is no longer present on the mature protein). As such, in some cases, a subject signal polypeptide is cleaved during processing of the surface accessible fusion protein (e.g., is no longer present on the mature protein that is displayed on the surface of the cell). In some cases, a signal polypeptide is one that is not cleaved during processing of the protein (i.e., is present in the mature protein).

A subject signal polypeptide can be native to the host cell in which it is expressed, or can be heterologous to the host cell, as long as it is operable to effect transport of the surface accessible fusion protein into the secretory pathway. A subject signal polypeptide can be a well characterized signal sequence, or can be any signal polypeptide derived from any protein of the secretory pathway. In some cases, a subject signal polypeptide is a synthetic signal polypeptide, i.e., the sequence is not present in (is modified relative to) a naturally existing protein.

In some embodiments, a subject surface accessible fusion protein includes a signal polypeptide from a protein (or is derived from a protein) that enters the ER via a post-translational route (referred to herein as a post-translational signal polypeptide). In some embodiments, a subject surface accessible fusion protein includes a signal polypeptide from a protein (or is derived from a protein) that enters the ER via a pre-translational route (referred to herein as a pre-translational signal polypeptide).

Numerous signal sequences suitable for the subject compositions, kits, and methods are known to those of ordinary skill in the art, and any convenient signal polypeptide can be used. For example, one of ordinary skill in the art will be able to readily identify signal polypeptides for use in the subject compositions, kits, and methods. Any convenient signal polypeptide can be used that is functional in a host cell of interest (e.g., a eukaryotic cell, a mammalian cell, a fungal cell, a yeast cell, etc.). Selection of a signal sequence can take into account, for example, the desired level of protein to be displayed at the surface of the cell (e.g., the yeast cell). For example the signal sequence from alpha mating factor can be useful when a high level of displayed protein is desired, but in some cases less protein is desired at the cell surface and in such cases, other signal polypeptides can be used (e.g., the signal peptides from Pho5p, Suc2p, etc.).

In some cases, the signal polypeptide is a heterologous polypeptide relative to the cell type in which the surface accessible fusion protein will be expressed. For example, if a surface accessible fusion protein will be expressed in a yeast cell, the signal polypeptide can be from (e.g., can be derived from) a cell type other than a yeast cell (e.g., a mammalian cell, a vertebrate cell, an invertebrate cell, etc.), or from a yeast cell of a different species from the species in which the surface accessible fusion protein will be expressed.

In some cases, the signal polypeptide is from (e.g., derived from) the same cell type that the surface accessible fusion protein will be expressed (e.g., in some cases from the same species). For example, if a surface accessible fusion protein will be expressed in a yeast cell, the signal polypeptide can be from a yeast protein (e.g., in some cases from the same species of yeast). Example signal polypeptides include, but are not limited to those from (or derived from) the following yeast proteins: mating factor alpha, Aga2p, Pho5p, and Suc2p.

Examples of suitable signal polypeptides include, but are not limited to, the following:

```
Signal polypeptide from Mating factor alpha:
                                         (SEQ ID NO: 11)
MRFPSIFTAVLFAASSALAAPANTTTEDETAQIPAEAVIDYSDLEGDFDA
AALPLSNSTNNGLSSTNTTIASIAAKEEGVQLDKREA Signal polypeptide from Mating factor alpha
(shorter):
                                         (SEQ ID NO: 12)
MRFPSIFTAVLFAASSALAA Signal polypeptide from Aga2p
                                         (SEQ ID NO: 13)
MQLLRCFSIFSVIASVLAQ Signal polypeptide from Pho5p
                                         (SEQ ID NO: 14)
MFKSVVYSILAASLANAG Signal polypeptide from Suc2p
                                         (SEQ ID NO: 15)
MLLQAFLFLLAGFAAKISAS Signal polypeptide from Cecropin-A (from
Hyalophora cecropia (Cecropia moth)):
                                         (SEQ ID NO: 16)
MNFSRIFFFVFACLTALAMVNA Signal polypeptide from GenBank AIO03624.1
                                         (SEQ ID NO: 17)
MRAFLALIFLTFVMNVESS
```

In some cases, the signal polypeptide includes an amino acid sequence having 60% or more amino acid sequence identity (70% or more, 75% or more, 80% or more, 85% or more, 90% or more, 95% or more, 98% or more, 99% or more, 99.5% or more, 99.8% or more, 99.9% or more, or 100% amino acid sequence identity) with the amino acid sequence set forth in any of SEQ ID NOs: 11-17.

As described in more detail below, in some cases, a surface anchor polypeptide includes a TM domain (e.g., a type II TM domain) that is positioned such that the surface accessible fusion protein is a type II membrane protein (i.e., the surface anchor polypeptide would be positioned near the N-terminus instead of the C-terminus of the surface accessible fusion protein). As would be readily understood by one of ordinary skill in the art, in such cases, a surface accessible fusion protein can include a signal polypeptide that is appropriate for type II membrane protein.

Protein of Interest

The term "protein of interest", "POI", or "polypeptide of interest" as used herein refers to any amino acid sequence of interest. In some cases, a POI is an entire protein (e.g., an entire protein that is naturally existing, a modified version of an entire protein, etc.). In some cases, a POI is a fragment of a protein, and can be any fragment of interest. For example, if one desires to investigate the binding or function of a particular portion of a protein (e.g., a domain, an extracellular domain, a protein binding domain, an enzymatic domain, an epitope, a portion of a protein with no known function or suspected function, etc.), the particular portion of interest can be referred to as a POI. The protein from which a POI is derived can be any protein (e.g., an antibody, a ligand, and receptor, a membrane protein, a secreted protein, an intracellular protein, an protein the localized to a particular organelle, a cytosolic protein, an enzyme, and the like). A POI can be naturally existing sequence or a non-naturally existing sequence (e.g., a synthetic amino acid sequence, a mutated/modified version of a naturally existing sequence, etc.).

In some cases, multiple POIs (e.g., two or more different POIs) are used in a subject method. In some cases, at least two of the two or more different POIs are similar to each other. For example, in some cases, the subject methods are screening methods that can be used to identify variants that bind with greater or weaker affinity to a particular compound. Thus multiple POIs can be used that are variants of one another (e.g., produced by mutagenesis). In some cases, at least two of the two or more POIs differ in amino acid sequence by 1 to 20 amino acids (e.g., 1 to 19 amino acids, 1 to 18 amino acids, 1 to 17 amino acids, 1 to 16 amino acids, 1 to 15 amino acids, 1 to 14 amino acids, 1 to 13 amino acids, 1 to 12 amino acids, 1 to 11 amino acids, 1 to 10 amino acids, 1 to 9 amino acids, 1 to 8 amino acids, 1 to 7 amino acids, 1 to 6 amino acids, 1 to 5 amino acids, 1 to 4 amino acids, 1 to 3 amino acids, 1 to 2 amino acids, or 1 amino acid).

Stalk Polypeptide

A "stalk polypeptide", also referred to herein as a "synthetic stalk polypeptide" is a synthetic sequence (a non-naturally occurring sequence) designed to provide clearance for the POI from the cell surface, and to be inert such that the POI and the stalk polypeptide do not interact. The stalk polypeptide is meant to provide an attachment for a POI to the cell surface while allowing the POI to fold (and in some cases function) free of influence from the surface. In addition, the use of a synthetic stalk polypeptide (e.g., in some cases in addition to a synthetic surface anchor polypeptide such as a synthetic GPI polypeptide) can ensure that undesired recombination does not occur within the yeast genome between yeast genomic sequences and nucleotides sequences encoding the synthetic stalk (and/or the synthetic surface anchor polypeptide).

Design features that can be used in designing a stalk polypeptide include low complexity in amino acid sequence, overall acidic character of the polypeptide, high hydrophilicity of the polypeptide, an absence of defined secondary or tertiary structure features within the polypeptide, a high density of O-linked glycosylation sites, and low self-similarity in the nucleotide sequence encoding the stalk polypeptide. In some cases, all of these features are taken into account such that the stalk polypeptide is characterized by low amino acid sequence complexity, overall acidic character, high hydrophilicity, an absence of defined secondary or tertiary structural features, a high density of O-linked glycosylation sites, and the nucleotide sequence encoding the stalk polypeptide is characterized by low self-similarity. In some cases, a stalk polypeptide comprises an amino acid sequence that is heavily O-glycosylated upon expression in a eukaryotic cell (e.g., a yeast cell). In some cases, a subject stalk polypeptide (and nucleotide sequences encoding the stalk polypeptide) can take into account (i.e., include) any or all of the above features (e.g., in any combination).

As noted above, in some cases, a stalk polypeptide comprises an amino acid sequence that is heavily O-glycosylated upon expression in a eukaryotic cell (e.g., a yeast cell). In some cases, a stalk polypeptide (e.g., a synthetic stalk polypeptide) comprises an amino acid sequence having 1 or more regions (e.g., 2 or more, 3 or more, 4 or more, 5 or more, 6 or more, or 7 or more regions) having 2 to 5 O-linked glycosylation sites (e.g., 2 to 4, 2 to 3, 3 to 5, 3 to 4, 4 to 5, 2, 3, 4, or 5 O-linked glycosylation sites) over a span of 5 amino acids. In some cases, a stalk polypeptide (e.g., a synthetic stalk polypeptide) comprises an amino acid sequence having 1 or more regions (e.g., 2 or more, 3 or more, 4 or more, 5 or more, 6 or more, or 7 or more regions) having 2 to 5 O-linked glycosylation sites (e.g., 2 to 4, 2 to 3, 3 to 5, 3 to 4, 4 to 5, 2, 3, 4, or 5 O-linked glycosylation sites) over a span of 10 amino acids. In some cases, a stalk polypeptide (e.g., a synthetic stalk polypeptide) comprises an amino acid sequence having 1 or more regions (e.g., 2 or more, 3 or more, 4 or more, 5 or more, 6 or more, or 7 or more regions) having 2 to 5 O-linked glycosylation sites (e.g., 2 to 4, 2 to 3, 3 to 5, 3 to 4, 4 to 5, 2, 3, 4, or 5 O-linked glycosylation sites) over a span of 20 amino acids. In some cases, a stalk polypeptide (e.g., a synthetic stalk polypeptide) comprises an amino acid sequence having 1 or more regions (e.g., 2 or more, 3 or more, 4 or more, 5 or more, 6 or more, or 7 or more regions) having 2 to 5 O-linked glycosylation sites (e.g., 2 to 4, 2 to 3, 3 to 5, 3 to 4, 4 to 5, 2, 3, 4, or 5 O-linked glycosylation sites) over a span of 50 amino acids. In some cases, a stalk polypeptide (e.g., a synthetic stalk polypeptide) comprises an amino acid sequence having 1 or more regions (e.g., 2 or more, 3 or more, 4 or more, 5 or more, 6 or more, or 7 or more regions) having 2 to 5 O-linked glycosylation sites (e.g., 2 to 4, 2 to 3, 3 to 5, 3 to 4, 4 to 5, 2, 3, 4, or 5 O-linked glycosylation sites) over a span of 100 amino acids. In some cases, a stalk polypeptide (e.g., a synthetic stalk polypeptide) comprises an amino acid sequence having 1 or more regions (e.g., 2 or more, 3 or more, 4 or more, 5 or more, 6 or more, or 7 or more regions) having 2 to 5 O-linked glycosylation sites (e.g., 2 to 4, 2 to 3, 3 to 5, 3 to 4, 4 to 5, 2, 3, 4, or 5 O-linked glycosylation sites) over a span of 200 amino acids.

In some cases, a stalk polypeptide (e.g., a synthetic stalk polypeptide) comprises an amino acid sequence having one or more O-linked glycosylation sites (e.g., 2 or more, 3 or more, 4 or more, 5 or more, 6 or more, 7 or more, 8 or more, 9 or more, or 10 or more O-linked glycosylation sites). In some cases, a stalk polypeptide (e.g., a synthetic stalk polypeptide) comprises an amino acid sequence having 1 to 10 O-linked glycosylation sites (e.g., 1 to 9, 1 to 8, 1 to 7, 2 to 10, 2 to 9, 2 to 8, or 2 to 7 O-linked glycosylation sites).

In some cases, a stalk polypeptide (e.g., a synthetic stalk polypeptide) comprises an amino acid sequence having 1 or more O-linked glycosylation sites (e.g., 1.2 or more, 1.4 or more, 1.6 or more, 1.8 or more, 2 or more, 2.2 or more, 2.4 or more, 2.6 or more, 2.8 or more, or 3 or more O-linked glycosylation sites) per 20 amino acids. In some cases, a stalk polypeptide (e.g., a synthetic stalk polypeptide) comprises an amino acid sequence having 1 or more O-linked glycosylation sites (e.g., 1.2 or more, 1.4 or more, 1.6 or more, 1.8 or more, 2 or more, 2.2 or more, 2.4 or more, 2.6 or more, 2.8 or more, or 3 or more O-linked glycosylation sites) per 40 amino acids. In some cases, a stalk polypeptide (e.g., a synthetic stalk polypeptide) comprises an amino acid sequence having 1 or more O-linked glycosylation sites (e.g., 1.2 or more, 1.4 or more, 1.6 or more, 1.8 or more, 2 or more, 2.2 or more, 2.4 or more, 2.6 or more, 2.8 or more, or 3 or more O-linked glycosylation sites) per 50 amino acids. In some cases, a stalk polypeptide (e.g., a synthetic stalk polypeptide) comprises an amino acid sequence having 0.5 or more O-linked glycosylation sites (e.g., 0.6 or more, 0.7 or more, 0.8 or more, 0.9 or more, 1 or more, 1.1 or more, 1.2 or more, 1.3 or more, 1.5 or more, or 2 or more O-linked glycosylation sites) per 100 amino acids. In some cases, a stalk polypeptide (e.g., a synthetic stalk polypeptide) comprises an amino acid sequence having 1 or more O-linked glycosylation sites (e.g., 1.2 or more, 1.4 or more, 1.6 or more, 1.7 or more, 1.8 or more, 2 or more, 2.2 or more, 2.4 or more, 2.6 or more, 2.8 or more, or 3 or more O-linked glycosylation sites) per 100 amino acids. In some cases, a stalk polypeptide (e.g., a synthetic stalk polypeptide) comprises an amino acid sequence having 0.5 or more O-linked glycosylation sites (e.g., 0.6 or more, 0.7 or more, 0.8 or more, 0.9 or more, 1 or more, 1.1 or more, 1.2 or more, 1.3 or more, 1.5 or more, or 2 or more O-linked glycosylation sites) per 200 amino acids. In some cases, a stalk polypeptide (e.g., a synthetic stalk polypeptide) comprises an amino acid sequence having 1 or more O-linked glycosylation sites (e.g., 1.2 or more, 1.4 or more, 1.6 or more, 1.7 or more, 1.8 or more, 2 or more, 2.2 or more, 2.4 or more, 2.6 or more, 2.8 or more, or 3 or more O-linked glycosylation sites) per 200 amino acids.

A stalk polypeptide can be of any desired length. For example, in some cases, a stalk polypeptide comprises a polypeptide sequence having a length in a range of from 10 to 2000 amino acids (e.g., from 20 to 2000 amino acids, from 50 to 2000 amino acids, from 20 to 1500 amino acids, from 50 to 1500 amino acids, from 20 to 1000 amino acids, from 50 to 1000 amino acids, from 20 to 800 amino acids, from 50 to 800 amino acids, from 100 to 2000 amino acids, from 100 to 1500 amino acids, from 100 to 1000 amino acids, from 100 to 800 amino acids, from 10 to 100 amino acids, from 20 to 100 amino acids, from 40 amino acids to 100 amino acids, from 101 to 200 amino acids, from 201 to 300 amino acids, from 301 to 400 amino acids, from 401 to 500 amino acids, from 501 to 600 amino acids, from 601 to 700 amino acids, from 701 to 800 amino acids, from 801 to 900 amino acids, from 901 to 1000 amino acids, from 1001 to 1500 amino acids, or from 1501 to 2000 amino acids). In some cases, a stalk polypeptide comprises a polypeptide sequence having a length of 10 or more amino acids (e.g., 20 or more, 30 or more, 40 or more, 50 or more, 60 or more, 70 or more, 80 or more, 90 or more, 100 or more, 125 or more, 150 or more, 200 or more, 250 or more, 300 or more, 350 or more, 400 or more, 450 or more, or 500 or more amino acids).

In some cases, the length of the stalk polypeptide can be used to make the surface accessible fusion protein accessible to agents of a defined molecular weight. For example, if the stalk polypeptide is short (e.g, 100 amino acids or less), then a larger agent may not have access to the POI of the surface accessible fusion protein due to steric hindrance. Thus, the length of the stalk polypeptide can be "tuned" to match a desired agent. For example, if one was going to screen a compound library for binding to a given POI, but they were only interested in compounds below a certain molecular weight (a threshold molecular weight), then a stalk polypeptide of a certain length can be chosen to provide steric hindrance to compounds above that threshold molecular weight. In other words, steric accessibility to a given POI can be "tuned" to a desired molecular weight cutoff by selecting a stalk polypeptide of an appropriate length. The greater the length of the stalk polypeptide, the less steric hindrance, and the greater accessibility (i.e., as the length of the stalk polypeptide increases, so too does the size of agent that can be used to bind to the POI of the surface accessible fusion protein). For an illustrative example, see the working examples below (FIGS. 1A-1C and FIG. 2A-2B).

Suitable stalk polypeptides include, but are not limited to, the examples provided here:

```
S19 (19 amino acids)
                                        (SEQ ID NO: 31)
GGGGSGGGGSGSTGGGGGS S41 (41 amino acids)
                                        (SEQ ID NO: 32)
QTSSPSREASVSTSSTSSSASQSSDPTTTSSSTVSTPATGA S232 (232 amino acids)
                                        (SEQ ID NO: 33)
QTSSPSTEASVSTSSTSSSASQSSDPTTTSSSSSSSSPSSQSEEISSSPT

VSTTPSTSSSSSSMTSTTTTKSISTSTTSSAPVTDVTVSSSPSKSTSTST

STETSKTPTSMTEYTSSTSIISTPVSHSQTGLSASSSSSSTTSGSSSTKS

ESSTTSGSSQSVESTSSHATVLANSAEMVTTSSSSSSTSEMSLTSTATSV

PVSSSSSTTYSTSASTQAVTTTSSSTVSTTSS

S465 (465 amino acids)
                                         (SEQ ID NO: 34
QTSSPSTEASVSTSSTSSSASQSSDPTTTSSSSSSSSPSSQSEEISSSPT

VSTTPSTSSSSSSMTSTTTTKSISTSTTSSAPVTDVTVSSSPSKSTSTST

STETSKTPTSMTEYTSSTSIISTPVSHSQTGLSASSSSSSTTSGSSSTKS

ESSTTSGSSQSVESTSSHATVLANSAEMVTTSSSSSSTSEMSLTSTATSV

PVSSSSSTTYSTSASTQAVTTTSSSTVSTTSSSTTLTSAFTHSSTTSSDQ

PPSDTTSPSTTHEPHVTTQTSSETSSSKSSSTSSSSTSQTSESATPSDSV

SPGSSTSTSSSSTSTSTSISSGETTTSSSSSSATTTSNSATLSVSTTQTS

IEASSSTTSTSSSTITTSSSSAHISSKSQSSITYPSSSTSSSTSSSISSE

SESFESTSAEDAPSTAPSSSVSSKSSTSTTSSTSTSSSTPSPSPSSVSSS

STSSLTTSAVSTPAT

S649 (649 amino acids)
                                        (SEQ ID NO: 35)
QTSSPSTEASVSTSSTSSSASQSSDPTTTSSSSSSSSPSSQSEEISSSPT

VSTTPSTSSSSSSMTSTTTTKSISTSTTSSAPVTDVTVSSSPSKSTSTST

-continued
STETSKTPTSMTEYTSSTSIISTPVSHSQTGLSASSSSSSTTSGSSSTKS

ESSTTSGSSQSVESTSSHATVLANSAEMVTTSSSSSSTSEMSLTSTATSV

PVSSSSSTTYSTSASTQAVTTTSSSTVSTTSSSTTLTSAFTHSSTTSSDQ

PPSDTTSPSTTHEPHVTTQTSSETSSSKSSSTSSSSTSQTSESATPSDSV

SPGSSTSTSSSSTSTSTSISSGETTTSSSSSSATTTSNSATLSVSTTQTS

IEASSSTTSTSSSTITTSSSSAHISSKSQSSITYPSSSTSSSTSSSISSE

SESFESTSAEDAPSTAPSSSVSSKSSTSTTSSTSTSSSTPSPSPSSVSSS

STSSLTTSAVSTPATSHSQSTVVTTTTITTSTGPVMSTTTAYSSSSTSSS

ESSEVQSVMSSTPSSTSTTTSSESTSSSSTASTSPSTSQTFETSPTIGGV

PSTTSFVSTPTTKLSHTTSTMTAQSDSKSTHSSSTSTEDKSSTASAVDES

TTTSTSTESTTSVTSGTSHSAKESSSNSKVYSSQTAHSSISVASSPSTK
```

In some cases, a subject synthetic stalk polypeptide includes an amino acid sequence having 60% or more amino acid sequence identity (70% or more, 75% or more, 80% or more, 85% or more, 90% or more, 95% or more, 98% or more, 99% or more, 99.5% or more, 99.8% or more, 99.9% or more, or 100% amino acid sequence identity) with the amino acid sequence set forth in any of SEQ ID NOs: 31-35 (e.g., 32-35, 33-35, 34-35). In some cases, a subject synthetic stalk polypeptide includes an amino acid sequence having 60% or more amino acid sequence identity (70% or more, 75% or more, 80% or more, 85% or more, 90% or more, 95% or more, 98% or more, 99% or more, 99.5% or more, 99.8% or more, 99.9% or more, or 100% amino acid sequence identity) with the amino acid sequence set forth in any of SEQ ID NOs: 32-35. In some cases, a subject synthetic stalk polypeptide includes an amino acid sequence having 60% or more amino acid sequence identity (70% or more, 75% or more, 80% or more, 85% or more, 90% or more, 95% or more, 98% or more, 99% or more, 99.5% or more, 99.8% or more, 99.9% or more, or 100% amino acid sequence identity) with the amino acid sequence set forth in any of SEQ ID NOs: 33-35.

Surface Anchor Polypeptide

A subject surface anchor polypeptide of a surface accessible fusion protein anchors the fusion protein to the cell surface. In some cases, the surface anchor polypeptide is (or is derived from) a Glycosylphosphatidylinisotol (GPI) anchor domain. A wide range of cell-surface proteins, including enzymes, coat proteins, surface antigens, and adhesion molecules, are attached to plasma membranes via GPI anchors (Burikofer et al. 2002 FASEB J 15:545). GPI is a post-translationally added lipid anchor; therefore, unlike conventional polypeptide anchors which have different transmembrane domains and connect to specific cytoplasmic extensions, GPI anchors use a common lipid structure to attach to the membrane, which is irrespective of the proteins linked with it (Englund et al., Annul Rev. Biochem. 62:121 (1993)). GPI-anchored proteins are synthesized as precursors with a cleavable, hydrophobic signal sequence at or near the N-terminus that targets the protein to the lumen of the endoplasmic reticulum (ER), and a cleavable signal sequence (GPI anchor domain) at or near the C-terminus that directs GPI anchoring. When a GPI anchor is added to a protein having a GPI anchor domain, all or a portion of the GPI anchor domain is cleaved off from the protein, and a GPI anchor is attached to the protein. A GPI anchor domain includes a hydrophobic region separated from the GPI-attachment site (omega-site) by a hydrophilic spacer region.

GPI anchored proteins have been identified throughout a broad range of eukaryotic species ranging from humans to insects, yeasts, bacteria, and fungi. GPI anchor domains have been identified for many proteins (for example, see Cares et al., Science 243:1196 (1989)). The GPI anchor signals have been successfully engineered onto the C-terminus of other proteins, and these GPI anchored proteins are coated on the cell surface and are functional. (Anderson et al., P.N.A.S. 93:5894 (1996); Brunschwig et al., J. Immunother. 22:390 (1999)).

Examples of suitable GPI anchor domains include, but are not limited to, those disclosed in the following references: Doering, T. L. et al. (1990) J. Biol. Chem. 265:611-614; McConville, M. J. et al. (1993) Biochem. J. 294:305-324; and PCT Publication WO 2003017944; all of which are hereby incorporated by reference in their entirety.

Any convenient GPI anchor domain can be used as a surface anchor polypeptide. Examples of GPI surface anchor polypeptides useful for the subject methods and compositions (e.g., GPI sequences found in *S. cerevisiae* proteins) include, but are not limited to:

```
                                             (SEQ ID NO: 51)
IQQNFTSTSLMISTYEGKASIFFSAELGSIIFLLLSYLLF (SEQ ID NO: 52)
EKSTNSSSSATSKNAGAAMDMGFFSAGVGAAIAGAAAMLL (SEQ ID NO: 53)
SLLKSAASATSSSQSSSKSKGAAGIIEIPLIFRALAELYNLVL (SEQ ID NO: 54)
SSGASSSSSKSSKGNAAIMAPIGQTTPLVGLLTAIIMSIM (SEQ ID NO: 55)
AQANVSASASSSSSSKKSKGAAPELVPATSFMGVVAAVGVALL (SEQ ID NO: 56)
GPGEKARKNNAAPGPSNFNSIKLFGVTAGSAAVAGALLLL (SEQ ID NO: 57)
SSTGMLSPTSSSSTRKENGGHNLNPPFFARFITAIFHHI (SEQ ID NO: 58)
SSFSSSGGSSESTTKKQNAGYKYRSSFSFSLLSFISYFLL (SEQ ID NO: 59)
YKSTVNGKVASVMSNSTNGATAGTHIAYGAGAFAVGALLL (SEQ ID NO: 60)
SGNLTTSTASATSTSSKRNVGDHIVPSLPLTLISLLFAFI (SEQ ID NO: 61)
GKNGAKSQGSSKKMENSAPKNIFIDAFKMSVYAVFTVLFSIIF (SEQ ID NO: 62)
TGSSSASSSSKSKGVGNIVNVSFSQSGYLALFAGLISALL (SEQ ID NO: 63)
ASGSSTHKKNAGNALVNYSNLNTNTFIGVLSVISAVFGLI (SEQ ID NO: 64)
EDADEDKDDLKRKHRNSASISGPLLPLGLCLLFFTFSLFF
```

Proteins from which a GPI surface anchor polypeptides can be from (e.g., derived from) include, but are not limited to: mating type protein agglutinin-a-1 (Aga1), flocculin proteins (e.g., Flo1), Sed1, Cwp1, Cwp2, Tip1, Tir1/Srp1, CCW14, CIS3, CWP1, PIR1, and PIR3. In some cases, a subject surface anchor polypeptide comprises an amino sequence having 60% or more amino acid sequence identity (60% or more, 70% or more, 80% or more, 90% or more, 92% or more, 95% or more, or 100% amino acid sequence identity) with the amino acid sequence set forth in any of SEQ ID NOs: 51-64. In some cases, a subject surface anchor polypeptide comprises an amino sequence having 60% or more amino acid sequence identity (60% or more, 70% or more, 80% or more, 90% or more, 92% or more, 95% or more, or 100% amino acid sequence identity) with the amino acid sequence set forth in SEQ ID NO: 51.

In some cases, the surface anchor polypeptide is heterologous (e.g., a GPI anchor domain from a different species or from a different organism relative to the host cell in which the surface accessible fusion protein will be expressed). The use of a heterologous surface anchor polypeptide (e.g., in some cases in addition to a synthetic stalk polypeptide) can decrease the likelihood that undesired recombination will occur within the yeast genome between yeast genomic sequences and nucleotide sequences encoding the heterologous surface anchor polypeptide (and/or the synthetic stalk polypeptide).

In some cases, the surface anchor polypeptide is a synthetic polypeptide (i.e., the surface anchor polypeptide comprises an amino acid sequence that is not naturally occurring). The use of a synthetic surface anchor polypeptide (e.g., a synthetic GPI anchor domain)(in some cases in addition to a synthetic stalk polypeptide) can decrease the likelihood that undesired recombination will occur within the yeast genome between yeast genomic sequences and nucleotide sequences encoding the synthetic surface anchor polypeptide (and/or the synthetic stalk polypeptide).

An example of a suitable synthetic (e.g., a hybrid) GPI surface anchor polypeptide is:

```
                                             (SEQ ID NO: 71)
     QIQSSMVEISTYAGSANSVNAGAGAGALFLLLSLAII.
```

In some cases, a subject surface anchor polypeptide (e.g., a GPI anchor domain) comprises an amino sequence having 60% or more amino acid sequence identity (60% or more, 70% or more, 75% or more, 80% or more, 85% or more, 90% or more, 92% or more, 95% or more, or 100% amino acid sequence identity) with an amino acid sequence (GPI anchor domain amino acid sequence) set forth in any of SEQ ID NOs: 51-64 and 71. In some cases, a subject synthetic surface anchor polypeptide comprises an amino sequence having 60% or more amino acid sequence identity (60% or more, 70% or more, 75% or more, 80% or more, 85% or more, 90% or more, 92% or more, 95% or more, or 100% amino acid sequence identity) with the amino acid sequence set forth in SEQ ID NO: 71. In some cases, a subject synthetic surface anchor polypeptide comprises the amino acid sequence set forth in SEQ ID NO: 71.

Thus, in some cases, a surface accessible fusion protein includes a GPI anchor domain as a surface anchor polypeptide. As such, a GPI anchor domain can be positioned C-terminal to both the signal polypeptide and the stalk polypeptide. In such cases, the POI would be positioned N-terminal to the stalk polypeptide and C-terminal to the signal polypeptide (e.g., between the signal polypeptide and the stalk polypeptide). Thus, in some cases (e.g., when the surface accessible fusion protein includes a GPI anchor domain as the surface anchor polypeptide), the components of the surface accessible fusion protein include, from N-terminal to C-terminal, a signal polypeptide, a POI, a stalk polypeptide (e.g., a synthetic stalk polypeptide), and a surface anchor polypeptide (e.g., a GPI anchor domain). Thus, in some cases, a display moiety (as discussed below) and/or a surface accessible fusion protein includes a GPI anchor domain as a surface anchor polypeptide. In some cases, the surface accessible fusion protein can also include one or more tags, as discussed in more detail below.

In some embodiments, the surface anchor polypeptide comprises a transmembrane (TM) domain (e.g., a transmembrane helix) that inserts into the plasma membrane of a cell.

In some cases, a surface accessible fusion protein is a type I membrane protein (e.g., has a type I TM domain as a surface anchor polypeptide). As such, a TM domain can be positioned C-terminal to both the signal polypeptide and the stalk polypeptide. In such cases, the POI would be positioned N-terminal to the stalk polypeptide and C-terminal to the signal polypeptide (e.g., between the signal polypeptide and the stalk polypeptide). In other words, in such cases, the TM domain would be positioned near the C-terminus of the surface accessible fusion protein, and the POI and stalk polypeptide would both be positioned N-terminal to the TM domain. Thus, in some cases (e.g., when the surface accessible fusion protein is a type I membrane protein and includes a TM domain as the surface anchor polypeptide), the components of the surface accessible fusion protein include, from N-terminal to C-terminal, a signal polypeptide, a POI, a stalk polypeptide (e.g., a synthetic stalk polypeptide), and a surface anchor polypeptide (e.g., a TM domain, a type I TM domain). Thus, in some cases, a display moiety (as discussed below) and/or a surface accessible fusion protein includes a type I TM domain as a surface anchor polypeptide. In some cases, the surface accessible fusion protein can also include one or more tags, as discussed in more detail below.

In some cases, a surface accessible fusion protein is a type II membrane protein (e.g., has a type II TM domain as a surface anchor polypeptide). As such, a TM domain can be positioned C-terminal to the signal polypeptide, and N-terminal to the stalk polypeptide. In such cases, the POI would be positioned C-terminal to the stalk polypeptide. In other words, in such cases, the TM domain would be positioned near the N-terminus of the surface accessible fusion protein, and the stalk polypeptide and the POI would both be positioned C-terminal to the TM domain. Thus, in some cases (e.g., when the surface accessible fusion protein is a type II membrane protein and includes a TM domain as the surface anchor polypeptide), the components of the surface accessible fusion protein include, from N-terminal to C-terminal, a signal polypeptide, a surface anchor polypeptide (e.g., a TM domain, a type II TM domain), a stalk polypeptide (e.g., a synthetic stalk polypeptide), and a POI. Thus, in some cases, a display moiety (as discussed below) and/or a surface accessible fusion protein includes a type II TM domain as a surface anchor polypeptide. In some cases, the surface accessible fusion protein can also include one or more tags, as discussed in more detail below.

Tags

In some cases, a subject surface accessible fusion protein includes a tag. The term "tag" as used herein is a polypeptide comprising an amino acid sequence that is detectable (directly and/or indirectly) and provides for ease of tracking and/or purification. Examples of suitable tags will be known to one of ordinary skill in the art and any convenient tag can be used. Examples of suitable tags include, but are not limited to directly detectable tags (e.g., a fluorescent polypeptide, e.g., green fluorescent protein (GFP), YFP, RFP, CFP, mCherry, tdTomato, and the like); and affinity tags (e.g. a histidine tag, e.g., a 6×His tag; a hemagglutinin (HA) tag; a FLAG tag; a Myc tag; and the like). In some cases, a surface accessible fusion protein includes more than one tag. Thus, in some cases a subject surface accessible fusion protein includes a one or more tags (2 or more, 3 or more, or 4 or more tags, or 1, 2, 3, or 4 tags).

A tag can be positioned anywhere within a surface accessible fusion protein. For example, a tag can be positioned: (i) C-terminal to the signal polypeptide and N-terminal to the POI; and/or (ii) C-terminal to the POI and N-terminal to the synthetic stalk polypeptide. In cases where a surface accessible fusion protein has more than one tag, the tags can be positioned on either end of the POI (e.g., one or more positioned C-terminal to the signal polypeptide and N-terminal to the POI, and one or more positioned C-terminal to the POI and N-terminal to the synthetic stalk polypeptide). In some cases, the tags are positioned in succession (i.e., next to one another).

Surface Accessible Fusion Proteins

A subject surface accessible fusion protein is a single protein that includes multiple components (e.g., a protein composed of polypeptide components that are modular and are linked together by peptide linkages, such that they constitute a single protein). The various components (e.g., signal polypeptide, POI, tag, stalk polypeptide, surface anchor polypeptide) of a subject surface accessible fusion protein can be linked one directly after the other (with no intervening amino acids), or can be separated by linker amino acids (e.g., any number of linker amino acids). For example, in some cases, there are no amino acids separating two given components of a subject surface accessible fusion protein. In some cases, there are one or more amino acids (e.g., 2 or more, 3 or more, 4 or more, 5 or more, 6 or more, 7 or more, 8 or more, 9 or more, 10 or more, 15 or more, 20 or more, 25 or more, 30 or more, or 40 or more amino acids) separating two given components of a subject surface accessible fusion protein. In some cases, there are 20 or less amino acids (e.g., 15 or less, 10 or less, 9 or less, 8 or less, 7 or less, 6 or less, 5 or less, 4 or less, 3 or less, or 2 or less amino acids) separating two given components of a subject surface accessible fusion protein.

In some cases, a subject surface accessible fusion protein consists of a signal polypeptide, a POI, a stalk polypeptide, and a surface anchor polypeptide. In some cases, a subject surface accessible fusion consists of a signal polypeptide, a POI, a stalk polypeptide, a surface anchor polypeptide, and one or more tags. In some cases, a subject surface accessible fusion protein consists essentially of a signal polypeptide, a POI, a stalk polypeptide, and a surface anchor polypeptide. In some cases, a subject surface accessible fusion consists essentially of a signal polypeptide, a POI, a stalk polypeptide, a surface anchor polypeptide, and one or more tags.

Two illustrative examples of suitable surface accessible fusion proteins are depicted below. In the two examples, CV1 is the POI to be displayed. It is a previously described engineered protein that binds CD47 with high affinity. In the following two examples, CV1 is displayed on yeast cells as a surface accessible fusion protein, tethered to a 649 amino acid stalk and one of two different GPI anchors:

```
"CV1 pYDS649HM"
Signal sequence: Mating-factor alpha leader
(amino acids 1-87)
                                        (SEQ ID NO: 11)

Protein of interest: CV1 (amino acids 90-208)
                                         (SEQ ID NO: 7)

HA epitope tag (amino acids 211-219)
                                         (SEQ ID NO: 8)

Stalk: 649 amino acid stalk (amino acids 220-868)
                                        (SEQ ID NO: 35)

Surface anchor: Hybrid GPI anchor domain (amino
acids 871-907)
                                        (SEQ ID NO: 71)

(SEQ ID NO: 9)
MRFPSIFTAVLFAASSALAAPANTTTEDETAQPAEAVDYSDLEGDFDAAA

LPLSNSTNNGLSSTNTTIASIAAKEEGVQLDKREASAEEELQIIQPDKSV

LVAAGETATLRCTITSLFPVGPIQWFRGAGPGRVLIYNQRQGPFPRVTTV
```

-continued

SDTTKRNNMDFSIRIGNITPADAGTYYCIKFRKGSPDDVEFKSGAGTELS

VRAKPSGSYPYDVPDYAQTSSPSTEASVSTSSTSSSASQSSDPTTTSSSS

SSSSPSSQSEEISSSPTVSTTPSTSSSSSSMTSTTTTKSISTSTTSSAPV

TDVTVSSSPSKSTSTSTSTETSKTPTSMTEYTSSTSIISTPVSHSQTGLS

ASSSSSSTTSGSSSTKSESSTTSGSSQSVESTSSHATVLANSAEMVTTSS

SSSSTSEMSLTSTATSVPVSSSSSTTYSTSASTQAVTTTSSSTVSTTSSS

TTLTSAFTHSSTTSSDQPPSDTTSPSTTHEPHVTTQTSSETSSSKSSSTS

SSSTSQTSESATPSDSVSPGSSTSTSSSSTSTSTSISSGETTTSSSSSSA

TTTSNSATLSVSTTQTSIEASSSTTSTSSSTITTSSSSAHISSKSQSSIT

YPSSSTSSSTSSSISSESESFESTSAEDAPSTAPSSSVSSKSSTSTTSST

STSSSTPSPSPSSVSSSSTSSLTTSAVSTPATSHSQSTVVTTTTITTSTG

PVMSTTTAYSSSSTSSSESSEVQSVMSSTPSSTSTTTSSESTSSSSTAST

SPSTSQTFETSPTIGGVPSTTSFVSTPTTKLSHTTSTMTAQSDSKSTHSS

STSTEDKSSTASAVDESTTTSTSTESTTSVTSGTSHSAKESSSNSKVYSS

QTAHSSISVASSPSTKGAQIQSSMVEISTYAGSANSVNAGAGAGALFLLL

SLAII

"CV1 pYDS649alphaM"
Signal sequence: Mating-factor alpha leader
(amino acids 1-87)
(SEQ ID NO: 11)

Protein of interest: CV1 (amino acids 90-208)
(SEQ ID NO: 7)

HA epitope tag (amino acids 211-219)
(SEQ ID NO: 8)

Stalk: 649 amino acid stalk (amino acids 220-868)
(SEQ ID NO: 35)

Surface anchor: Agg1p GPI anchor domain: (amino
acids 871-910)
(SEQ ID NO: 51)

(SEQ ID NO: 10)
MRFPSIFTAVLFAASSALAAPANTTTEDETAQIPAEAVIDYSDLEGDFDA

AALPLSNSTNNGLSSTNTTIASIAAKEEGVQLDKREASAEEELQIIQPDK

SVLVAAGETATLRCTITSLFPVGPIQWFRGAGPGRVLIYNQRQGPFPRVT

TVSDTTKRNNMDFSIRIGNITPADAGTYYCIKFRKGSPDDVEFKSGAGTE

LSVRAKPSGSYPYDVPDYAQTSSPSTEASVSTSSTSSSASQSSDPTTTSS

SSSSSSPSSQSEEISSSPTVSTTPSTSSSSSSMTSTTTTKSISTSTTSSA

PVTDVTVSSSPSKSTSTSTSTETSKTPTSMTEYTSSTSIISTPVSHSQTG

LSASSSSSTTSGSSSTKSESSTTSGSSQSVESTSSHATVLANSAEMVTT

SSSSSSTSEMSLTSTATSVPVSSSSSTTYSTSASTQAVTTTSSSTVSTTS

SSTTLTSAFTHSSTTSSDQPPSDTTSPSTTHEPHVTTQTSSETSSSKSSS

TSSSSTSQTSESATPSDSVSPGSSTSTSSSSTSTSTSISSGETTTSSSSS

SATTTSNSATLSVSTTQTSIEASSSTTSTSSSTITTSSSSAHISSKSQSS

ITYPSSSTSSSTSSSISSESESFESTSAEDAPSTAPSSSVSSKSSTSTTS

STSTSSSTPSPSPSSVSSSSTSSLTTSAVSTPATSHSQSTVVTTTTITTS

TGPVMSTTTAYSSSSTSSSESSEVQSVMSSTPSSTSTTTSSESTSSSSTA

STSPSTSQTFETSPTIGGVPSTTSFVSTPTTKLSHTTSTMTAQSDSKSTH

SSSTSTEDKSSTASAVDESTTTSTSTESTTSVTSGTSHSAKESSSNSKVY

SSQTAHSSISVASSPSTKGAIQQNFTSTSLMISTYEGKASIFFSAELGSI

IFLLLSYLLF

Nucleic Acids

Aspects of the disclosure include nucleic acids for expressing a surface accessible fusion protein, nucleic acids encoding a surface accessible fusion protein, and methods of using the nucleic acids (e.g., to express a surface accessible fusion protein on the surface of a cell, for screening for compounds that bind to a surface accessible fusion protein, for screening for polypeptides that bind to a compound of interest, and the like). In some cases, a subject nucleic acid is a recombinant expression vector (e.g., for expressing a subject surface accessible fusion protein).

In some cases, a subject nucleic acid for expressing a surface accessible fusion protein does not include a nucleotide sequence encoding a protein of interest (POI). For example, the nucleic acid can be a pre-cursor for inclusion of a POI (e.g., between the nucleotide sequences encoding the signal polypeptide and the stalk polypeptide). For example, the nucleic acid can include a nucleotide sequence that encodes a signal polypeptide, a stalk polypeptide, and a surface anchor polypeptide (and in some cases a tag), all of which are operably linked to the same promoter where the promoter is functional in a eukaryotic host cell of interest (e.g., a eukaryotic cell, a mammalian cell, a fungal cell, a yeast cell, a *S. cerevisiae* cell, etc.), but the nucleic acid might not include nucleotides encoding a POI. In some cases, such a nucleic acid is a recombinant expression vector.

In some cases, the nucleic acid (e.g, a recombinant expression vector) includes an insert site for the insertion of a POI. For example, an insertion site for inserting nucleotides encoding a POI can exist between nucleotides encoding a signal polypeptide and a stalk polypeptide (signal:stalk junction), a signal polypeptide and a tag (signal:tag junction) a tag and a stalk polypeptide (tag:stalk junction), and/or a first tag and a second tag (tag:tag junction). In some cases, an insertion site for inserting nucleotides encoding a POI is positioned adjacent to nucleotide encoding a stalk polypeptide.

Insertion sites for use with various technologies are known to those of ordinary skill in the art and any convenient insertion site can be used. In other words, an insertion site can be for any method for manipulating nucleic acid sequences. For example, in some cases the insertion site can be a multiple cloning site (e.g., a site including one or more restriction enzyme sites), a site for ligation independent cloning, a site for recombination based cloning (e.g., recombination based on att sites), a nucleotide sequence recognized by a CRISPR (e.g. Cas9) based technologies, and the like. In some cases, an insertion site can be defined by the junction of the nucleotides encoding one component of a subject surface accessible fusion protein with the nucleotides encoding another component of the subject surface accessible fusion protein (e.g., signal:stalk junction, tag:stalk junction, and/or tag:tag junction) such that there exist no intervening nucleotides. An insertion site can be of any desired length and does not have to be in frame with the 3' components (e.g., nucleotides encoding the stalk polypeptide and the surface anchor polypeptide) because the intent of an insertion site is that it will get modified (e.g., in some cases replaced) to include a nucleotide sequence encoding a protein of interest. One of ordinary skill in the art will appreciate that once nucleotides encoding a POI are inserted at an insertion site, they need to be in frame with both the upstream sequences (e.g., sequences encoding the signal polypeptide) and the downstream sequences (e.g., sequences encoding the stalk polypeptide and the surface anchor polypeptide).

Thus, in some cases, a subject nucleic acid (for expressing a polypeptide of interest on the surface of a cell) includes a nucleotide sequence that encodes a display moiety. A "display moiety" as used herein, refers to a combination of components of a subject surface accessible fusion protein, other than the POI. For example, a display moiety can include a signal polypeptide, a stalk polypeptide (e.g., a synthetic stalk polypeptide), and a surface anchor polypeptide (not necessarily in that order). In some cases, in order from N-terminal to C-terminal, a display moiety includes a signal polypeptide, a stalk polypeptide (e.g., a synthetic stalk polypeptide), and a surface anchor polypeptide (e.g., a GPI anchor domain, a type I TM domain, etc.). In some cases, in order from N-terminal to C-terminal, a display moiety includes a signal polypeptide, a surface anchor polypeptide (e.g., a type II TM domain, a TM domain from a type II membrane protein, etc.), and a stalk polypeptide (e.g., a synthetic stalk polypeptide). When a subject nucleic acid does not include a POI (e.g., when the nucleic acid includes an insertion site for a POI, when the nucleic acid is intended to be used for the insertion of a nucleotide sequence encoding a POI, etc.), the nucleotides encoding the components of the display moiety need not be in frame with one another prior to the insertion of the nucleotide sequence encoding the PO. For example, they can be in frame with one another after the insertion of the nucleotide sequence encoding a POI such that the encoded surface accessible fusion protein includes the components of the display moiety (i.e., a signal polypeptide, a stalk polypeptide, and a surface anchor polypeptide; the order of which can vary depending on the nature of the surface anchor polypeptide as described above). In such cases, the nucleic acid can still be referred to as a nucleic acid that includes nucleotide sequences encoding a display moiety.

In some cases, a subject display moiety includes a signal polypeptide, a stalk polypeptide, and a surface anchor polypeptide. In some cases, a subject display moiety includes a signal polypeptide, a stalk polypeptide, a surface anchor polypeptide, and one or more tags. In some cases, a subject display moiety consists of a signal polypeptide, a stalk polypeptide, and a surface anchor polypeptide. In some cases, a subject display moiety consists of a signal polypeptide, a stalk polypeptide, a surface anchor polypeptide, and one or more tags. In some cases, a subject display moiety consists essentially of a signal polypeptide, a stalk polypeptide, and a surface anchor polypeptide. In some cases, a subject display moiety consists essentially of a signal polypeptide, a stalk polypeptide, a surface anchor polypeptide, and one or more tags.

For example, in some cases, a subject nucleic acid (for expressing a polypeptide of interest on the surface of a cell) includes a nucleotide sequence that encodes (i) a first nucleotide sequence that encodes a signal polypeptide; (ii) a second nucleotide sequence that encodes a synthetic stalk polypeptide; and (iii) a third nucleotide sequence that encodes a surface anchor polypeptide. In some cases, (i), (ii), and (iii) are positioned relative to one another in a 5' to 3' orientation and are operably linked to the same promoter, where the promoter is functional in a host cell (e.g., a eukaryotic cell, a vertebrate cell, an invertebrate cell, a mammalian cell, a fungal cell, a yeast cell, etc.). In some such cases, the nucleic acid includes an insertion site (described above) for inserting a nucleotide sequence that encodes a protein of interest (POI), where the insertion site is positioned 3' of (i) and 5' of (ii). In some cases, the nucleic acid also includes a nucleotide sequence that encodes a tag (e.g., positioned such that it is in frame with at least one of the nucleotide sequences that encode the other components [(i), (ii), and (iii)].

In some cases (e.g., when a subject nucleic acid includes a nucleotide sequence that encodes a display moiety), (i), (ii), and (iii) above are positioned relative to one another in a 5' to 3' orientation, in the order: (i), (iii), and (ii) (e.g., when the surface anchor polypeptide is a TM domain and the surface accessible fusion protein will be a type II membrane protein) and are operably linked to the same promoter, where the promoter is functional in a host cell (e.g., a eukaryotic cell, a vertebrate cell, an invertebrate cell, a mammalian cell, a fungal cell, a yeast cell, etc.). In some such cases, the nucleic acid includes an insertion site (described above) for inserting a nucleotide sequence that encodes a protein of interest (POI), where the insertion site is positioned 3' of (ii). In some cases, the nucleic acid also includes a nucleotide sequence that encodes a tag (e.g., positioned such that it is in frame with at least one of the nucleotide sequences that encode the other components [(i), (ii), and (iii)].

Nucleic acids encoding a surface accessible fusion protein include a nucleotide sequence that encodes a surface accessible fusion protein (a fusion protein having a signal polypeptide, a protein of interest (POI), a stalk polypeptide, and a surface anchor polypeptide)(and in some cases a tag). In some cases, the nucleotide sequence that encodes a surface accessible fusion protein is operably linked to a promoter that is functional in a eukaryotic host cell of interest (e.g., a eukaryotic cell, a mammalian cell, a fungal cell, a yeast cell, a S. cerevisiae cell, etc.).

As such, in some cases, a subject nucleic acid (e.g., encoding a surface accessible fusion protein) includes (i) a first nucleotide sequence that encodes a signal polypeptide; (ii) a second nucleotide sequence that encodes a protein of interest (POI); (iii) a third nucleotide sequence that encodes a synthetic stalk polypeptide; and (iv) a fourth nucleotide sequence that encodes a surface anchor polypeptide. In some such cases, (i), (ii), (iii), and (iv) are positioned, from 5' to 3', in order [(i), (ii), (iii), and (iv)], and are in frame with one another such that they collectively encode a surface accessible fusion protein that includes the signal polypeptide, the POI, the stalk polypeptide, and the surface anchor polypeptide (e.g., in some cases in that order). In some cases, the encoded surface accessible fusion protein also includes a tag such that the nucleic acid includes a nucleotide sequence that encodes that tag. In some cases nucleotide sequence encoding the surface accessible fusion protein is operably linked to a promoter that is functional in a eukaryotic host cell of interest (e.g., a eukaryotic cell, a mammalian cell, a fungal cell, a yeast cell, a S. cerevisiae cell, etc.).

In some cases, a subject nucleic acid (e.g., encoding a surface accessible fusion protein) includes (i) a first nucleotide sequence that encodes a signal polypeptide; (ii) a second nucleotide sequence that encodes a surface anchor polypeptide (e.g., a TM domain when the surface accessible fusion protein is a type II membrane protein); (iii) a third nucleotide sequence that encodes a synthetic stalk polypeptide; and (iv) a fourth nucleotide sequence that encodes a protein of interest (POI). In some such cases, (i), (ii), (iii), and (iv) are positioned, from 5' to 3', in order [(i), (ii), (iii), and (iv)], and are in frame with one another such that they collectively encode a surface accessible fusion protein that includes the signal polypeptide, the surface anchor polypeptide, the stalk polypeptide, and the POI (e.g., in some cases in that order). In some cases, the encoded surface accessible fusion protein also includes a tag such that the nucleic acid includes a nucleotide sequence that encodes that tag. In some cases nucleotide sequence encoding the surface accessible fusion protein is operably linked to a promoter that is functional in a eukaryotic host cell of interest (e.g., a eukaryotic cell, a mammalian cell, a fungal cell, a yeast cell, a S. cerevisiae cell, etc.).

As used herein, a "promoter sequence" or "promoter" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include at least the minimum number of bases or elements necessary to initiate transcription at levels detectable above background. Within the promoter sequence will be found protein binding domains responsible for the binding of RNA polymerase. Eukaryotic promoters will often, but not always, contain "TATA" boxes and "CAT" boxes. Various promoters, including inducible promoters, may be used to drive the various vectors of the present invention. A promoter can be a constitutively active promoter (i.e., a promoter that is constitutively in an active/"ON" state). A promoter can be an inducible promoter (i.e., a promoter whose state, active/"ON" or inactive/"OFF", is controlled by an external stimulus, e.g., the presence of a particular temperature, compound, or protein).

Any convenient promoter can be used and many promoters are readily available to one of ordinary skill in the art. It will be appreciated that a promoter must be functional in the cell in which the surface accessible fusion protein is to be expressed (e.g., eukaryotic cell, fungal cell, yeast cell, vertebrate cell, mammalian cell, invertebrate cell, etc.). Examples of promoters useful in yeast expression vectors, include but are not limited to: AOX1 promoter, galactose inducible promoters (e.g., pGAL1, pGAL1-10, pGal4, pGal10, etc.), phosphoglycerate kinase (pPGK) promoter, cytochrome c (pCYC1) promoter, alcohol dehydrogenase I (pADH1) promoter, and the like.

Additional exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

Any of the above described nucleic acids can be a recombinant expression vector (which can include any convenient promoter for expressing a subject surface accessible fusion protein, including, but not limited to, any of the promoters described above). In some embodiments, a subject recombinant expression vector is operable in a host cell to direct the expression and display of a surface accessible fusion protein. In some embodiments, a subject recombinant expression vector is operable in a yeast cell to direct the expression and display of a surface accessible fusion protein.

A wide range of recombinant expression vectors are known in the art and available commercially which meet various requirements for recombinant gene expression in yeast. Most yeast vectors are shuttle vectors, which contain sequences permitting them to be selected and propagated in bacteria (e.g, E. coli), thus allowing for convenient amplification and subsequent alteration in vitro. Many common yeast shuttle vectors originated from pBR322. They contain an origin of replication promoting high copy-number maintenance in E. coli (e.g., ColE1 origin of replication), and a selectable antibiotic marker (e.g., the .beta.-lactamase gene, tetracycline resistance gene conferring resistance to, respectively, ampicillin and tetracycline). Specific yeast shuttle vectors include, but are not limited to those described in U.S. Pat. Nos. 5,866,404 and 6,897,353. Additional yeast vectors useful for practicing the methods described herein, for example, but not limited to, the expression of a subject surface accessible fusion protein in a species such as Pichia pastoris (i.e., a Pichia pastoris host cell), are described in U.S. Pat. Nos. 5,707,828, 6,730,499, U.S. Patent Publication No. 20060270041, and PCT Publication Nos. WO2005040395 and WO200231178.

Yeast vectors can contain marker genes that allow selection of transformants containing the desired plasmid. Examples of the most commonly used yeast marker genes include, but are not limited to, URA3, HIS3, LEU2, TRP1 and LYS2, which complement specific auxotrophic mutations in the host cell. The URA3 and LYS2 yeast marker genes have an additional advantage because they allow the use of both positive and negative selection schemes. Selectable marker genes conferring dominant drug resistant phenotype to the yeast host cell, such as the hph and nat genes conferring resistance to hygromycin B and nourseothricin, respectively (see, Sato et al., Yeast 22:583-591 (2005)) may also be used. Most currently used yeast shuttle vectors fall into one of the following three broad categories: (i) integrative vectors, (ii) autonomously replicating high copy-number vectors, or (iii) autonomously replicating low copy-number vectors.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Depending on the host/vector system utilized, any of a number of suitable transcription and translation control elements, including constitutive and inducible promoters, transcription enhancer elements, transcription terminators, etc. may be used in an expression vector (see e.g., Bitter et al. (1987) Methods in Enzymology, 153:516-544).

In some cases, the nucleotides encoding the components of a subject surface accessible fusion protein are operatively linked to a transcription terminator sequence (e.g. to facilitate proper mRNA processing). Thus, in some cases, a subject recombinant expression vector includes a terminator sequence. Examples of transcription termination elements (terminator sequences) include, but are not limited to, the termination sequences of several yeast genes, such as CYC1, ADH1, ARO4, TRP1, ACT1, AND YPT1. Any convenient termination sequence can be used.

One illustrative example of a subject DNA nucleic acid having a nucleotide sequence that encodes a subject surface accessible fusion protein is the 8584 nucleotide (nt) vector set forth in SEQ ID NO: 6. In this example, the signal polypeptide is mating factor alpha leader, which is encoded by nucleotides 856-1113 (SEQ ID NO: 1); the protein of interest (POI) is CV1, which is encoded by nucleotides 1123-1479 (SEQ ID NO: 2); the synthetic stalk polypeptide (649 amino acids) is encoded by nucleotides 1513-3459 (SEQ ID NO: 4); and the surface anchor polypeptide is a synthetic hybrid GPI sequence, which is encoded by nucleotides 3466-3576 (SEQ ID NO: 5). This example nucleic acid also has nucleotides that encode an HA epitope tag (nucleotides 1486-1512) (SEQ ID NO: 3).

Host Cells

Aspects of the disclosure include cells (i.e., host cells) that include the above described surface accessible fusion proteins and/or nucleic acids (e.g, nucleic acids for expressing surface accessible fusion proteins, and/or nucleic acids encoding surface accessible fusion proteins). The term "host cell" is used herein to refer to a cell in which a subject surface accessible fusion protein is to be expressed and displayed; or to refer to a cell in which a nucleic acid is to be propagated. A host cell can be used to express a subject surface accessible fusion protein from a subject nucleic acid such as a recombinant expression vector (e.g., a eukaryotic host cell) and/or to propagate a subject recombinant expression vector (e.g., a eukaryotic host cell or a prokaryotic host cell).

In some cases, a subject host cell is a prokaryotic cell. For example, in some cases, a subject recombinant expression vector (having nucleotides that encode a surface accessible fusion protein) is inside of a prokaryotic cell for the purposes of propagation and/or purification of the recombinant expression vector. As such, in some cases, a prokaryotic cell (e.g., a bacterial cell such as an *E. coli* cell) includes a nucleic acid (e.g. a recombinant expression vector) as described above.

In some cases, a suitable host cell is a cell of a single-cell eukaryotic organism, a fungal cell, a yeast cell, an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), etc.

In some cases, a suitable host cell is a fungal cell. Any fungal cell (e.g., any convenient species of fungus) is suitable. In some cases, a suitable host cell is a yeast cell. Any convenient species of yeast cell can be used. Illustrative examples of suitable yeast species (i.e., species of suitable yeast cell) include, but are not limited to: *Saccharomyces cerevisiae, Schizosaccharomyces pombe, Saccharomyces uvarium, Pichia pastoris* (syn. *Komagataella pastoris*), *Hansenula polymorpha* (syn. *Ogataea parapolymorpha*), *Yarrowia lipolytica, Pichia stipitis* (syn. *Scheffersomyces stipitis*), *Kluyveromyces marxianus, Pachysolen tannophilus, Candida boidinii, Candida albicans,* and *Candida sorenensi.*

Suitable methods for introducing nucleic acids (e.g., recombinant expression vectors) (also referred to as "transformation" and/or "transfection") include e.g., viral infection, transfection, lipofection, nucleofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. Any convenient method can be used.

The choice of method of introducing nucleic acid is generally dependent on the type of cell being transformed and the circumstances under which the transformation is taking place. For example, when transforming fungal cells such as yeast, protocols such as those utilizing lithium acetate, single-stranded carrier DNA, and/or PEG (in some cases coupled with heat shock) can be used. One of ordinary skill in the art would be readily able to determine an appropriate protocol for introducing a subject nucleic acid into a desired host cell. A general discussion of various transformation methods can be found in Ausubel, et al., Short Protocols in Molecular Biology, 3rd ed., Wiley & Sons, 1995.

For example, for viral vector delivery, cells are contacted with viral particles comprising a subject nucleic acid. Retroviruses, for example, lentiviruses, are particularly suitable. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing retroviral vectors having a nucleic acid of interest into packaging cell lines and of collecting the viral particles that are generated by the packaging lines are known in the art.

Methods

Aspects of the disclosure include methods of using the above described surface accessible fusion proteins and nucleic acids. Methods are provided for: (i) expressing a protein of interest (POI) in a eukaryotic cell (e.g., displaying a POI on the surface of a eukaryotic cell); (ii) measuring the binding of an agent to a POI (e.g., in some cases determining whether an agent can bind to a POI); (iii) identifying an agent (a compound) that binds to a POI (e.g., screening test compounds for an agent that binds to a POI); (iv) identifying a polypeptide that binds to an agent (e.g., a polypeptide that binds to agent when the agent is present at a particular concentration, e.g., to identify a polypeptide that binds to an agent with an affinity greater than or equal to a predetermined value); (v) generating a variant polypeptide that binds to an agent with an affinity that is different (e.g., greater) than the affinity of the polypeptide from which the variant was derived; and the like.

(i) Methods of Expressing

In some embodiments, the subject method is a method of expressing a protein of interest (POI) in a eukaryotic cell (e.g., displaying a POI on the surface of a eukaryotic cell). Such methods include introducing into a cell (e.g., any desired host cell) a subject surface accessible fusion protein that includes the POI. For example, such a method can include introducing into a eukaryotic cell (e.g., a host cell, as described above, such as a fungal cell, a yeast cell, a mammalian cell, etc.) a nucleic acid having a nucleotide sequence that encodes a surface accessible fusion protein, where the surface accessible fusion protein includes a signal polypeptide, a POI, a stalk polypeptide, and a surface anchor polypeptide (and in some cases a tag). A surface accessible fusion protein that includes the POI can be introduced into a cell: (i) directly as a protein (e.g., in some cases using a protein transduction domain); (ii) as an RNA encoding the protein; (iii) or as a DNA encoding the protein. In some cases (e.g., when the surface accessible fusion protein is introduced into a cell as DNA) the nucleotides encoding a surface accessible fusion protein are operably linked to a promoter that is operable in the cell.

In some cases, a method of expressing a protein of interest (POI) in a eukaryotic cell (e.g., displaying a POI on the surface of a eukaryotic cell) further includes any combination of steps of the methods described below.

(ii) Methods of Measuring the Binding

In some embodiments, the subject method is a method of measuring the binding of an agent to a POI (e.g., in some cases determining whether an agent can bind to a POI). Methods of measuring the binding of an agent to a POI can include displaying the POI on the surface of a eukaryotic cell (e.g., any eukaryotic host cell of interest, e.g., a mammalian cell, a fungal cell, a yeast cell, etc.)(e.g., see "methods of expressing" above).

Methods of measuring the binding of an agent to a POI include contacting the eukaryotic cell (the cell expressing the POI by displaying the POI on the surface of the cell as a surface accessible fusion protein) with an agent. An agent (also referred to herein as a "test compound") can be any agent that can bind to a POI. For example, suitable agents include any chemical entity, pharmaceutical, drug, peptide, antibody, antibody binding fragment, small molecule compound, including both known and potential therapeutic compounds, that can be tested (e.g., screened) for its potential binding to one or more POIs. For example, in some cases, the POI includes an antigen binding domain of an antibody and the agent (e.g., test agent) is a peptide (in some cases a variant of a peptide known to bind to the antibody). In some cases, the POI is an epitope (or a variant of a known epitope) for an antibody and the agent is the antibody or an antigen binding domain from the antibody. In some cases, the POI is the binding region of a ligand or receptor (or a variant thereof) of a ligand/receptor pair.

In some cases, the agent includes a detectable label (e.g., the agent can be directly or indirectly detectable). In some cases, the agent is directly labeled (e.g., the agent can include a directly detectable adduct, such as a fluorescent adduct). In some cases, the agent is indirectly labeled (e.g, the agent can include an indirectly detectable adduct, such as biotin).

In some cases, measuring the amount of the agent bound to the POI (i.e., bound to the surface accessible fusion protein) can be accomplished by measuring the amount of the agent (e.g., quantitatively or qualitatively, as described below) bound to the cell expressing the surface accessible fusion protein.

"Measuring an amount" as used herein can provide qualitative or quantitative results, and thus, the phrase as used herein encompasses quantitative as well as qualitative measures. For example, in some cases where measuring an amount is qualitative, measuring the amount of an agent bound to a POI includes determining whether an agent is bound or not bound to the POI (e.g., bound or not bound to a cell expressing a surface accessible fusion protein that includes the POI; present or not present at the end of the protocol, etc.). In some cases, measuring the amount of agent bound to a POI includes determining whether an agent is bound or not bound to the POI above a particular threshold of binding. Thus, in some cases, a step of measuring an amount includes is a step of determining whether an agent is bound or not bound to a POI (e.g., to a surface accessible fusion protein, to a cell expressing a surface accessible fusion protein, etc.). In some cases, measuring an amount provides a simple "yes" or "no" determination of whether an agent is present.

Likewise, in some embodiments, measuring an amount includes determining a quantitative measure of the amount of agent bound to a surface accessible fusion protein (e.g., using flow cytometry, ELISA, or any other method that can quantitatively measure the amount of agent present at the end of a given protocol, e.g., present after a final washing step). The amount (level) of agent bound can be expressed in arbitrary units associated with a particular assay (e.g., fluorescence units, e.g., mean fluorescence intensity (MFI)), or can be expressed as an absolute value with defined units (e.g., number of molecules (e.g., moles), number of protein molecules, concentration of agent, etc.). Additionally, a quantitatively measured amount (level) can be compared to the amount of a reference value to derive a normalized value that represents a normalized measured amount. Thus, a step of measuring an amount can be a detecting in a qualitative manner ("present" vs "absent"; "yes, above a predetermined threshold" vs "no, not above a predetermined threshold"; etc.) or a quantitative manner.

Techniques such as flow cytometry and ELISA can be used in both qualitative and quantitative steps of measuring. For example, both of the techniques can be used to determine a quantitative amount (e.g., in fluorescent units such as mean fluorescent intensity (MFI)) of an agent that is present, but can also be used to simply determine if the amount present is present above a particular threshold. (iii) Methods of Identifying an Agent In some embodiments, the subject method is a method of identifying an agent (a compound) that binds to a POI (e.g., screening test compounds for an agent that binds to a POI). Methods of identifying an agent that binds to a POI include displaying the POI on the surface of a eukaryotic cell (e.g., any eukaryotic host cell of interest, e.g., a mammalian cell, a fungal cell, a yeast cell, etc.), contacting the cell with an agent, and measuring the amount (quantitatively and/or qualitatively) of agent that is bound to the cell.

In some cases, a given surface accessible fusion protein can be displayed on the surface of two or more cells (e.g., on the surface of cells in two or more separate populations of cells), and each cell (e.g., each separate population of cells) is contacted with a different agent. Thus, two or more agents (e.g., a library of agents) can be screened to identify which, if any, of the agents binds to the cells expressing the POI as a surface accessible fusion protein.

As noted above, in some cases, the POI includes an antigen binding domain of an antibody and the agent (e.g., test agent) is a peptide (in some cases a variant of a peptide known to bind to the antibody); in some cases, the POI is an epitope (or a variant of a known epitope) for an antibody and the agent is the antibody or an antigen binding domain from the antibody; and in some cases, the POI is the binding region of a ligand or receptor (or a variant thereof) of a ligand/receptor pair. In some such cases, a method can include a step of mutagenesis (e.g., using any convenient method, such as random or site-directed PCR protocols). For example, two or more test agents (e.g., a library of test agents) can be generated (e.g. two or more agents that are variants of one another), and the agents can be used to contact cells expressing a subject surface accessible fusion protein, and those agents that bind to the cells can be identified.

In some cases, the concentration of an agent can be controlled so that only those agents that bind with a particular affinity (or better) will be identified. In some cases, different concentrations of a given agent can be used to contact each cell (e.g., separate populations of cells). As such, the methods can be used to determine whether the binding of an agent to a given POI is maintained at different concentrations of agent (which, for example, can be used to estimate an affinity of the agent for the POI). For example, an agent can be used at 10 nM, 100 nM, and 1000 nM to contact three different cell populations, each expressing the same surface accessible fusion protein. Whether or not the agent is bound can be determined for each concentration, and an estimate of binding affinity can be made. For example, an agent that binds at all three concentrations can be said to bind to a given POI with a higher affinity than an agent that binds at 1000 nM but does not bind at 100 nM or 10 nM.

In some cases, a cell expressing a surface accessible fusion protein can be contacted at the same time (simultaneously) with two or more agents, where the agents are distinguishable from one another (e.g., where each agent has a different detectable label). As an illustrative example, a given cell or population of cells can be contacted with 10 different agents, where each agent includes a different detectable label (e.g., a different fluorescent label). After the appropriate washes, the amount of each detectable label can be measured (quantitatively and/or qualitatively). For example, one may use such a method to pool multiple different agents to identify those that bind to the surface accessible fusion protein from those that don't.

(iv) Methods of Identifying a Polypeptide

In some embodiments, the subject method is a method of identifying a polypeptide that binds to an agent (e.g., a polypeptide that binds to agent when the agent is present at a particular concentration, e.g., to identify a polypeptide that binds to an agent with an affinity greater than or equal to a pre-determined value). Methods of identifying a polypeptide that binds to an agent include displaying the POI on the surface of a eukaryotic cell (e.g., any eukaryotic host cell of interest, e.g., a mammalian cell, a fungal cell, a yeast cell, etc.). Such methods can be identical to those above for methods of identifying an agent, but this case the used may be held constant (or used at particular concentrations), but the agent is used to contact two or more cells, where at least two of the two or more cells expresses (is displaying) a different POI in the form of a different surface accessible fusion protein. For each cell (or each population of cells), binding of the agent can be measured (qualitatively or quantitatively), and one can thereby determine which of the two or more POIs can bind to a given agent (or to a given concentration of a given agent).

(v) Methods of Generating a Variant Polypeptide

In some embodiments, the subject method is a method of generating a variant polypeptide that binds to an agent with an affinity that is different (e.g., greater) than the affinity of the polypeptide from which the variant was derived. Such methods include a step generating one or more variant polypeptides (e.g., using any convenient method to generate a variant, e.g., PCR based mutagenesis). For example, the variant polypeptides would be identical to the starting surface accessible fusion protein, with the exception that they would different by one or more amino acids at the POI portion of the surface accessible fusion protein. Measuring the amount of binding of an agent with one or more of the generated variants would then be used to identify which of the variants bind to the agent.

As noted above, in some cases, a POI includes an antigen binding domain of an antibody and the agent (e.g., test agent) is a peptide (in some cases a variant of a peptide known to bind to the antibody); in some cases, the POI is an epitope (or a variant of a known epitope) for an antibody and the agent is the antibody or an antigen binding domain from the antibody; and in some cases, the POI is the binding region of a ligand or receptor (or a variant thereof) of a ligand/receptor pair. In some such cases, a method can include a step of mutagenesis (e.g., using any convenient method, such as random or site-directed PCR protocols). For example, two or more POIs (two or more surface accessible fusion proteins) can be generated (e.g., to generate a library of surface accessible fusion proteins) (e.g., where the POIs are variants of one another and/or variants of a staring POI). An agent can then be used to contact cells (e.g., different populations of cells) expressing the two or more surface accessible fusion proteins (the variants), and those POIs that bind to the agent can then be identified.

Similar to the above, in some cases, the concentration of an agent can be controlled so that only those POIs that bind with a particular affinity (or better) to the agent will be identified. In some cases, different concentrations of a given agent can be used to contact the each cell (e.g., separate populations of cells, multiple copies of a library of cells, etc.). As such, the methods can be used to identify only those POIs that can bind to a given agent when the agent is present at a given concentration. As an illustrative example, one may contact two or more different POIs (via contacting cells expressing surface accessible fusion proteins) with an agent at a given concentration (e.g., 100 nM), and they may identify a large number of POIs that bind the agent. The POIs could then be re-screened using a lower concentration of agent (e.g., 10 nM), to limit the number of POIs identified.

For any or all of the above methods, various control may be used. For example, a surface accessible fusion protein having a control POI (or no POI) can be used to provide a control for the amount of signal expected in the absence of binding. Various such controls would be readily contemplated by one of ordinary skill in the art and any convenient control can be used.

Kits

Also provided are kits for use in the methods. The subject kits can include any of above described surface accessible fusion proteins and/or nucleic acids. For example, in some cases, a suitable kit includes a nucleic acid (e.g., a recombinant expression vector) for expressing a surface accessible fusion protein, or a nucleic acid (e.g., a recombinant expression vector) encoding a surface accessible fusion protein, as described above. In some cases, a kit includes two or more DNA nucleic acids (e.g., recombinant expression vectors).

In some cases, a kit includes two or more subject DNA nucleic acids (e.g., recombinant expression vectors) for expressing a surface accessible fusion protein. The kits can include nucleic acids that include nucleotides encoding a POI, nucleic acids that do not include nucleotides encoding a POI, nucleic acids that include an insertion site for inserting nucleotides encoding a POI, etc. In some cases, at least two of the two or more DNA nucleic acids include an insertion site for inserting a POI.

In some cases, the synthetic stalk polypeptides encoded by at least two of the two or more DNA nucleic acids are of different lengths. For example, in some cases, the stalk polypeptides (e.g., synthetic stalk polypeptides) encoded by at least two of the two or more DNA nucleic acids have a length in a range of: from 20 to 100 amino acids, from 40 amino acids to 100 amino acids, from 101 to 200 amino acids, from 201 to 300 amino acids, from 301 to 400 amino acids, from 401 to 500 amino acids, from 501 to 600 amino acids, from 601 to 700 amino acids, from 701 to 800 amino acids, from 801 to 900 amino acids, from 901 to 1000 amino acids, or from 1001 to 1500 amino acids. In some cases, the synthetic stalk polypeptides encoded by at least two of the two or more DNA nucleic acids are of different lengths and each have a length in a range of: from 20 to 100 amino acids, from 40 amino acids to 100 amino acids, from 101 to 200 amino acids, from 201 to 300 amino acids, from 301 to 400 amino acids, from 401 to 500 amino acids, from 501 to 600 amino acids, from 601 to 700 amino acids, from 701 to 800 amino acids, from 801 to 900 amino acids, from 901 to 1000 amino acids, or from 1001 to 1500 amino acids. As such, in some cases, a kit can include multiple DNA nucleic acids (e.g., for expressing a subject surface accessible fusion protein), where the stalk polypeptides encoded by multiple DNA nucleic acids span a range of lengths.

In some cases, the synthetic stalk polypeptides encoded by at least two of the two or more DNA nucleic acids have different sequences (e.g., even if they are of the same length).

As an illustrative example, one nucleic acid (e.g., recombinant expression) of a kit might encode a stalk polypeptide with a length in a range of from 20 to 100 amino acids, and another might encode a stalk polypeptide with a length in a range of from 101 to 200 amino acids. In other words, a kit may have multiple nucleic acids (e.g., recombinant expression vectors) encoding multiple different stalk polypeptides (e.g., differing by length and/or by sequence). Such a kit would allow one to perform the subject methods using multiple different surface accessible fusion proteins, even if in some cases the POI was the same for different fusion proteins. In the same vein, in some cases, at least two of the two or more DNA nucleic acids encode different signal polypeptides, different tags (and/or a different arrangement of tags, i.e., different positioning of the nucleotides encoding the tags relative to the other encoded components), and/or different surface anchor polypeptides (e.g., different GPI anchors). In some cases, at least two of the two or more DNA nucleic acids have different insertion sites. Any or all combinations of the above are contemplated.

Any of the above-described kits can further include one or more additional reagents, where such additional reagents can be selected from: a dilution buffer; a reconstitution solution; a wash buffer; a control reagent; a control expression vector; a reagent; a host cell having a subject nucleic acid; a host cell not having a subject nucleic acid (e.g. a nucleic acid for expressing a surface accessible fusion protein, a nucleic acid encoding a surface accessible fusion protein, etc.), and the like. Components of a subject kit can be in separate containers (e.g., different tubes, different wells of a multiwell plate, etc.), and can in some cases be combined in a single container.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility

The compositions and methods described herein can be used to develop new fungal cells (e.g., new yeast strains) for various purposes, including but not limited to fermentative production of chemicals and polypeptides. In addition, the compositions and methods described herein may be used for a variety of research purposes, including the expression of mutagenized proteins or other combinatorial libraries on yeast. In contrast to other methods, the compositions and methods described herein use monocistronic vectors, enabling use in a wide variety of yeast strains and species. Moreover, the compositions and methods described herein allow selective ("tunable") accessibility to a protein of interest (e.g., by varying the length of the stalk polypeptide), which can controlled to limit the molecular weight of a substrate or binding partner. Expression of proteins on the surface of eukaryotic cells (e.g., fungal cells, yeast cells etc.) is widely used in industry for a diverse array of purposes. The compositions and methods described herein allow straightforward and simple expression of any desired protein (a protein of interest) fused to a synthetic stalk polypeptide. Because a POI can be displayed as part of a surface accessible fusion protein using a monocistronic vector, the system is readily portable to a variety of yeast strains and species.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Example 1

Figure 1B:
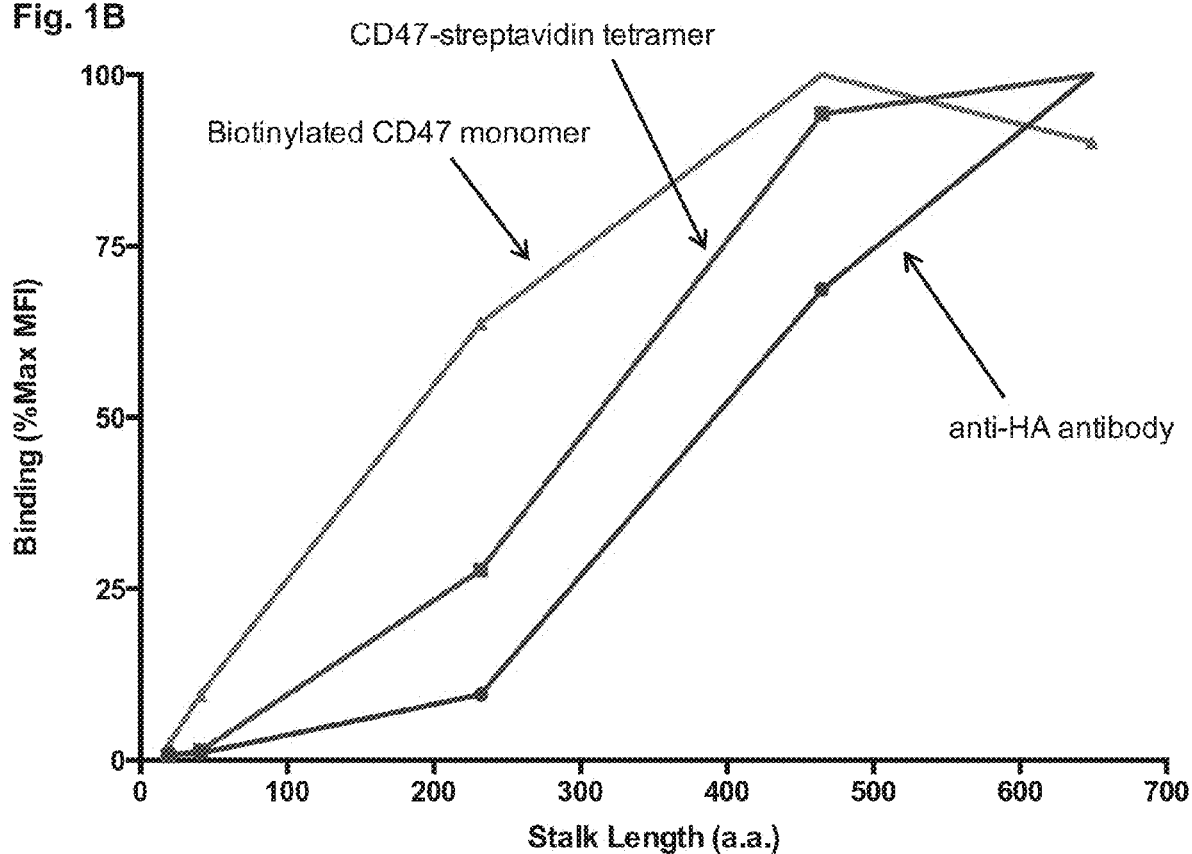
Figure 1C:
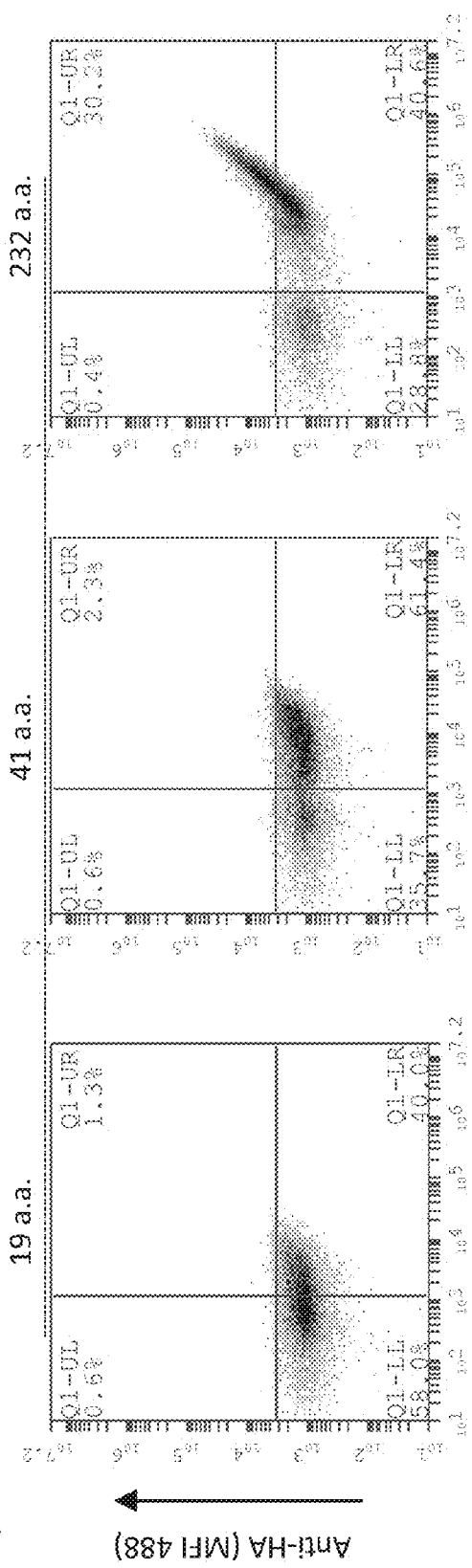
Figure 1C:
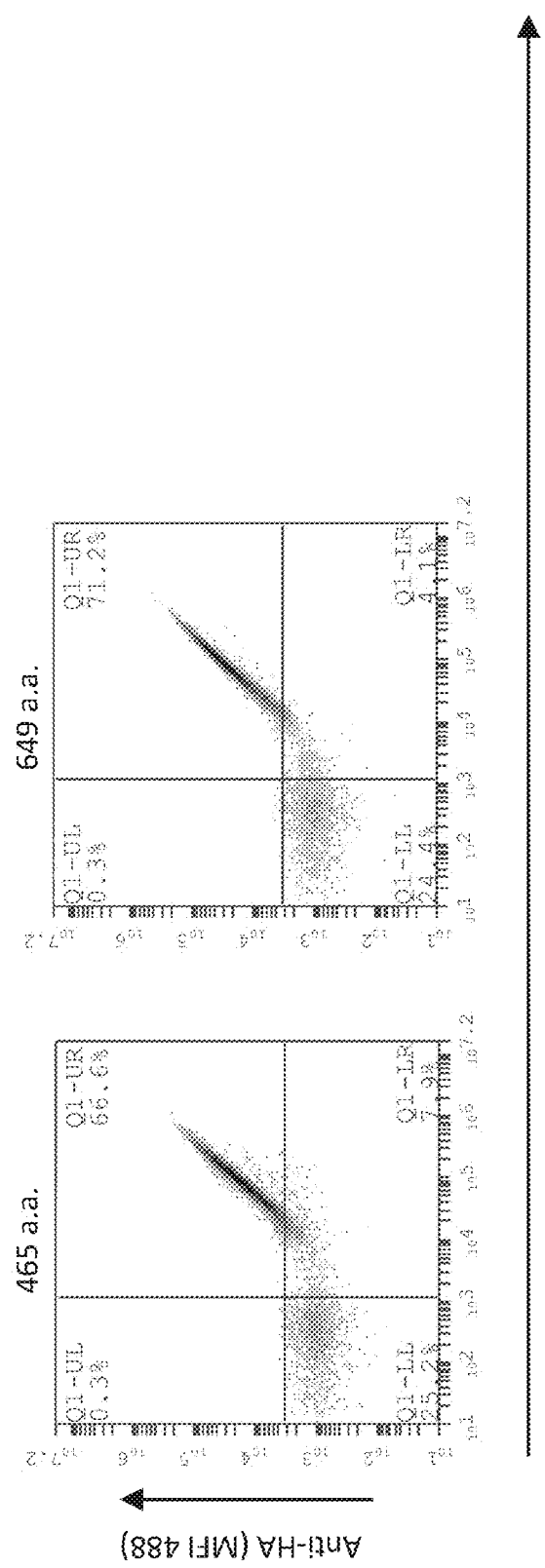

FIG. 1A-1C depicts experiments performed to determine whether accessibility could be "tuned" using variable-length GPI-anchored "stalk polypeptides." The yeast strain used for these experiments was BJ5465. FIG. 1A depicts a schematic of one embodiment of peptide linkage to the yeast cell surface: a protein of interest (POI) (here, the engineered SIRPa variant CV1) is secreted as a surface accessible fusion protein in which the POI is fused to (i) a signal polypeptide (which directs the protein to the secretory pathway, but which can be cleaved from the protein via post-translational processing), (ii) a stalk polypeptide (a synthetic sequence, the length of which can be modified over a wide range of lengths), (iii) a GPI anchor (e.g. a synthetic GPI anchor), and optionally (iv) an epitope tag (depicted is an HA epitope tag).

FIG. 1B depicts experimental results showing the relationship between stalk length (in amino acids) and surface staining for 3 labeled probes of different size (different molecular weight): anti-HA antibody (~150 kD), CD47-streptavidin tetramers (~100 kD)(which bind to CV1, the POI used in these experiments), and CD47-biotin monomers (~15 kDa) (which also bind to CV1). FIG. 1C depicts representative flow cytometry plots of yeast displaying CV-1 attached to different length stalks stained simultaneously with Anti-HA antibodies (Alexa488) and CD47-biotin monomers (Alexa647). The length of the tested stalk sequences, in number of amino acids, is listed above each plot. The data show that stalk length can be used to "select" for compounds of a particular molecular weight. For example, depicted on the Y-axis is binding of the 150 kD anti-HA antibody, which did not bind very well to the surface accessible fusion polypeptide when the stalk polypeptide was 19 or 41 amino acids in length, but did bind when the stalk polypeptide was 232, 465, or 649 amino acids in length. To the contrary, CD47-biotin (x-axis) bound to the surface accessible fusion polypeptide even when the stalk polypeptide was 19 amino acids in length, but bound stronger when the stalk polypeptide was 41, 232, 465, or 649 amino acids in length.

Figure 2A:
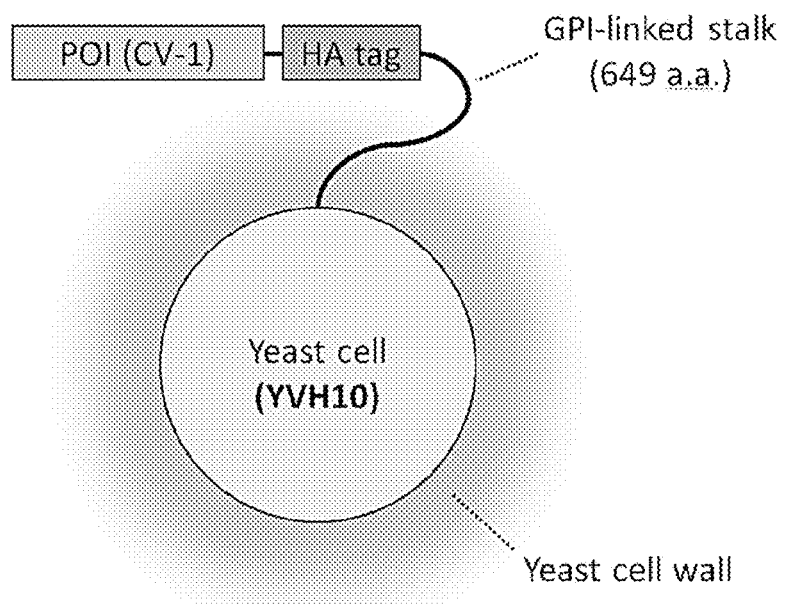
FIG. 2A-2B. The subject compositions and methods are compatible with additional yeast strains.
Figure 2B:
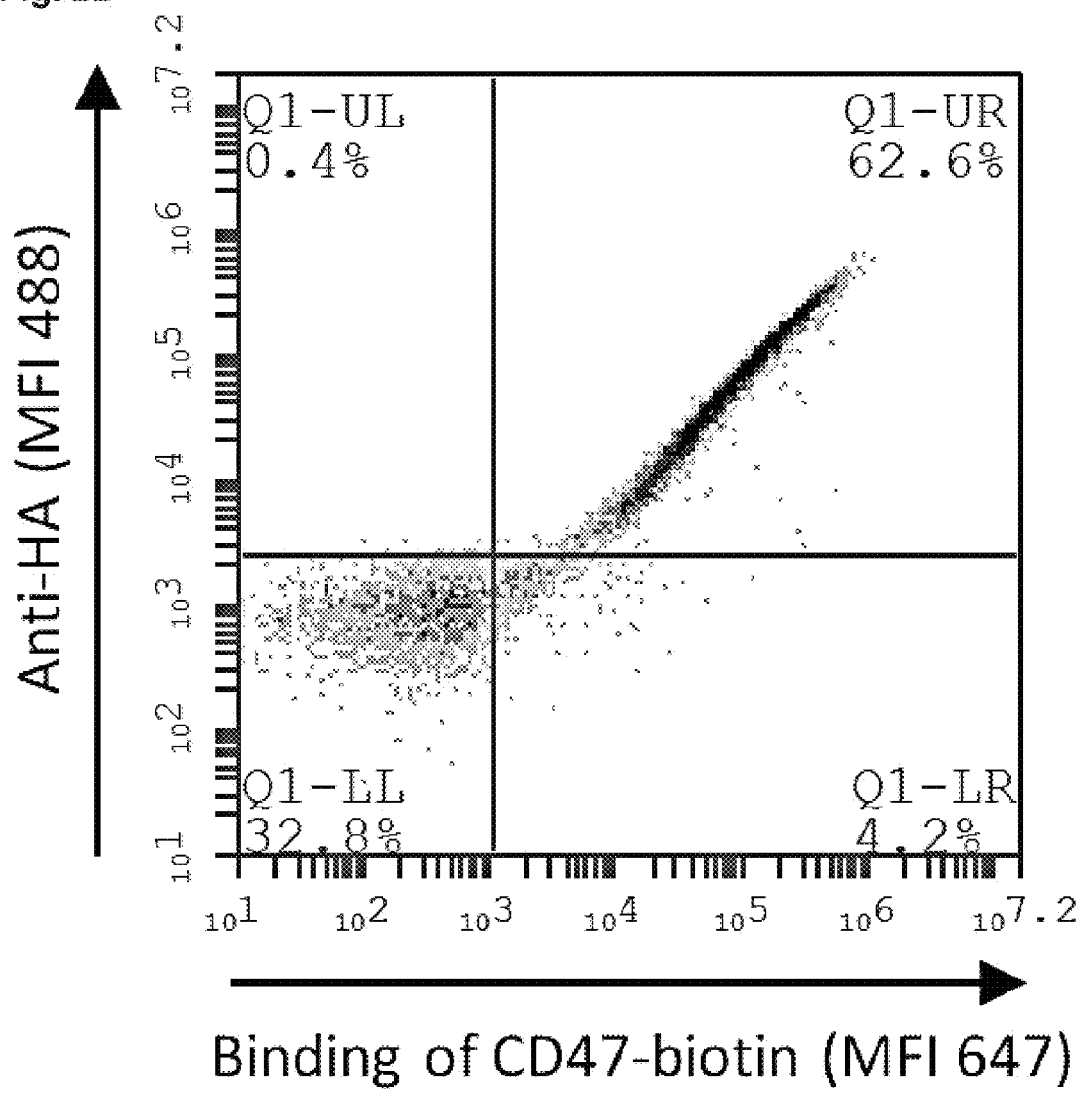

FIG. 2A-2B depicts experiments performed to determine whether the subject compositions and methods are compatible with additional yeast strains. A) Schematic of peptide linkage to the yeast cell surface. The engineered SIRPA variant CV1 was secreted as a fusion to the HA epitope tag and a 649 amino-acid long synthetic stalk with a synthetic GPI anchor (i.e, CV1 was the protein of interest (POI), which was expressed as a surface accessible fusion polypeptide). The yeast strain used for these experiments was YVH10, in contrast to BJ5465 used in FIG. 1A-1C. YVH10 yeast overexpress yeast protein disulfide isomerase (PDI), enabling greater folding capacity for secreted, disulfide-bond containing proteins. B) Representative flow cytometry plots of YVH10 yeast displaying CV-1 attached to a 649 amino acid stalks stained simultaneously with Anti-HA antibodies (Alexa488) and CD47-biotin monomers (Alexa647). Thus, the data demonstrate that the subject compositions and methods are in fact compatible with additional yeast strains.

Example 2: Directed Evolution of Human PD-L1 Protein for High-Affinity PD-1 Binding Objective:
to identify mutant variants of PD-L1 that bind to T cell-expressed PD-1 with high affinity and specificity, thereby acting as a competitive inhibitor of interactions with PD-L1 expressed on the surface of tumor cells or tumor-infiltrating immune cells.

Approach:

select a stable subunit of the human PD-L1 protein from the region that interacts with the PD-1 protein; select amino acid residues likely to be important for this interaction, and by PCR and Gibson cloning, generate a library of plasmids that encode mutant variants of PD-L1 attached to a GPI-linked anchor (as per the primary technology described in the patent); electroporate library of plasmids into yeast or fungal strain; induce surface display of mutant proteins; select for high-affinity binders by assessing interaction with a tagged, soluble, recombinant PD-1 protein; upon isolation of a pool of high-affinity PD-1 binders, extract DNA from the resulting yeast population and sequence the variants present; assess binding affinity of sequences and assemble consensus variant sequences to maximize binding affinity.

Example 3: Directed Evolution of a Soluble Fragment of Human IL2Rβ for High-Affinity Binding to IL-2

Objective:

to identify mutant variants of the cytokine receptor subunit IL2Rβ that bind to endogenous IL-2 with high affinity and specificity, thereby acting as a competitive sink to inactivate the interaction of IL-2 with endogenous IL-2 receptor complexes.

Approach:

select a stable subunit of the human IL2Rβ protein from the region that interacts with the IL-2 protein; select amino add residues likely to be important for this interaction, and by PCR and Gibson cloning, generate a library of plasmids that encode mutant variants of IL2Rβ attached to a GPI-linked anchor (as per the primary technology described in the patent); electroporate library of plasmids into yeast or fungal strain; induce surface display of mutant proteins; select for high-affinity binders by assessing interaction with a tagged, soluble, recombinant IL-2 protein; upon isolation of a pool of high-affinity IL-2 binders, extract DNA from the resulting yeast population and sequence the variants present; assess binding affinity of sequences and assemble consensus variant sequences to maximize binding affinity.

Example 4: Yeast Surface Display of Human Antibody Libraries

Objective:

to express human antibody binding domains, either as fragments of antigen binding (Fab) or single chain variable fragments (scFv), on the surface of yeast for the purpose of generating high-affinity, high-specificity therapeutic human monoclonal antibodies against any known cell surface or secreted protein.

Approach:

By gene synthesis, generate a library of plasmids that encode variants of human antibody binding regions (either in Fab or scFv format) fused to a GPI-linked anchor (as per the primary technology described in the patent); electroporate library of plasmids into yeast or fungal strain; induce surface display of antibody fragments; select for high-affinity binders by assessing interaction with a tagged, soluble, recombinant protein corresponding to the desired region of protein binding (for example, to generate a therapeutic antibody which would bind PD-1 and block its interaction with PD-L1, one would pan the library using a tagged fragment of PD-1 that included the interacting region with PD-L1); upon isolation of a pool of high-affinity binders, extract DNA from the resulting yeast population and sequence the antibody variants present; assess binding affinity of individual sequences as recombinant antibodies.

Example 5: Yeast Surface Display of Alternative Scaffold Libraries

Objective:

to express alternative scaffold libraries, including but not limited to fibronectins, immunoglobulins, knottins, DARPins, anticalins, on the surface of yeast for the purpose of generating high-affinity, high-specificity therapeutic human monoclonal antibodies against any known cell surface or secreted protein.

Approach:

By gene synthesis, generate a library of plasmids that encode variants of human antibody binding regions (either in Fab or scFv format) fused to a GPI-linked anchor (as per the primary technology described in the patent); electroporate library of plasmids into yeast or fungal strain; induce surface display of alternative scaffold proteins; select for high-affinity binders by assessing interaction with a tagged, soluble, recombinant protein corresponding to the desired region of protein binding (for example, to generate a therapeutic alternative scaffold protein which would bind PD-1 and block its interaction with PD-L1, one would pan the library using a tagged fragment of PD-1 that included the interacting region with PD-L1); upon isolation of a pool of high-affinity binders, extract DNA from the resulting yeast population and sequence the alternative scaffolds present; assess binding affinity of individual sequences as recombinant proteins.

Example 6: Yeast Surface Display of Translated cDNAs to Identify Interacting Proteins of a Target of Interest in an Unbiased Fashion Objective:

to express the proteins encoded by cDNA collections, for example from a tumor-derived cell line, or a normal cell type, on the surface of yeast for the purpose of panning with a protein of interest, in order to identify novel interacting partners based on binding to the protein of interest.

Approach:

By gene synthesis, generate a library of plasmids that encode cDNAs derived from a cell type of interest fused to a GPI-linked anchor (as per the primary technology described in the patent); electroporate library of plasmids into yeast or fungal strain; induce surface display of alternative scaffold proteins; select for high-affinity binders by assessing interaction with a tagged, soluble, recombinant protein of interest; upon isolation of a pool of yeast that express proteins that interact with the protein of interest, extract DNA from the resulting yeast population and sequence the alternative scaffolds present to identify the responsible cDNAs.

What is claimed is:

1. A DNA nucleic acid for expressing a polypeptide of interest on the surface of a cell, the nucleic acid comprising:
    (i) a first nucleotide sequence that encodes a signal polypeptide;
    (ii) a second nucleotide sequence that encodes a synthetic stalk polypeptide that comprises an amino acid sequence having 60% or more amino acid sequence identity with the amino acid sequence set forth in any of SEQ ID NOs: 31-35; and
    (iii) a third nucleotide sequence that encodes a surface anchor polypeptide,
    wherein (i), (ii), and (iii) are positioned relative to one another in a 5' to 3' orientation and are operably linked to the same promoter, wherein the promoter is functional in a eukaryotic cell.

2. The DNA nucleic acid of claim 1, comprising an insertion site for inserting a nucleotide sequence that encodes a protein of interest (POI), wherein the insertion site is positioned 3' of (i) and 5' of (ii).

3. The DNA nucleic acid of claim 1, comprising (iv) a fourth nucleotide sequence that encodes a protein of interest (POI), wherein said first through fourth nucleotide sequences are:
    (a) positioned, from 5' to 3', in the following order: (i), (iv), (ii), (iii); and
    (b) are in frame with one another such that they collectively encode a surface accessible fusion protein comprising the signal polypeptide, the POI, the stalk polypeptide, and the surface anchor polypeptide.

4. The DNA nucleic acid of claim 1, wherein the stalk polypeptide comprises a polypeptide sequence having a length of 20 or more amino acids.

5. The DNA nucleic acid of claim 1, wherein the stalk polypeptide comprises a polypeptide sequence having a length in a range of from 20 to 2000 amino acids.

6. The DNA nucleic acid of claim 1, wherein the signal polypeptide:
    is a signal polypeptide from a yeast protein;
    is from a protein that exhibits post-translational transport to the endoplasmic reticulum (ER); or
    comprises an amino acid sequence having 60% or more amino acid sequence identity with the amino acid sequence set forth in any of SEQ ID NOs: 11-17.

7. The DNA nucleic acid of claim 1, wherein the surface anchor polypeptide is a glycosylphosphatidylinositol (GPI) anchor domain.

8. The DNA nucleic acid of claim 7, wherein the GPI anchor domain comprises an amino acid sequence having 60% or more amino acid sequence identity with the amino acid sequence set forth in any of SEQ ID NOs: 51-64 and 71.

9. The DNA nucleic acid of claim 1, wherein the surface anchor polypeptide is a synthetic polypeptide sequence.

10. The DNA nucleic acid of claim 1, wherein the DNA nucleic acid is a recombinant expression vector.

11. The DNA nucleic acid of claim 1, wherein said promoter is functional in a fungal cell.

12. The DNA nucleic acid of claim 11, wherein the fungal cell is a yeast cell.

13. A kit, comprising two or more DNA nucleic acids, wherein each DNA nucleic acid comprises:
    (i) a first nucleotide sequence that encodes a signal polypeptide;
    (ii) a second nucleotide sequence that encodes a synthetic stalk polypeptide; and
    (iii) a third nucleotide sequence that encodes a surface anchor polypeptide,
    wherein (i), (ii), and (iii) of each DNA nucleic acid are positioned relative to one another in a 5' to 3' orientation and are operably linked to the same promoter;
    wherein at least one of the stalk polypeptides encoded by the two or more DNA nucleic acids comprises an amino acid sequence having 60% or more amino acid sequence identity with the amino acid sequence set forth in any of SEQ ID NOs: 31-35.

14. The kit of claim 13, wherein the stalk polypeptides encoded by at least two of the two or more DNA nucleic acids are of different lengths.

15. A protein, or a nucleic acid encoding the same, comprising a synthetic GPI anchor domain, wherein the synthetic GPI anchor domain comprises an amino acid sequence having 60% or more or 80% or more amino acid sequence identity with the amino acid sequence set forth in any of SEQ ID NOs: 51-64 and 71.

16. A method of displaying a protein of interest (POI) on the surface of a eukaryotic cell, the method comprising:
    introducing into a eukaryotic cell a DNA nucleic acid comprising a nucleotide sequence that: (i) is operably linked to a promoter that is functional in the eukaryotic cell, and (ii) encodes a surface accessible fusion protein, wherein the surface accessible fusion protein comprises, in order, a signal polypeptide, a POI, a synthetic stalk polypeptide, and a surface anchor polypeptide,
    wherein the synthetic stalk polypeptide comprises an amino acid sequence having 60% or more amino acid sequence identity with the amino acid sequence set forth in any of SEQ ID NOs: 31-35.

17. The method according to claim 16, wherein the eukaryotic cell is a fungal cell.

18. The method according to claim 17, wherein the fungal cell is a yeast cell.

19. A method of measuring the binding of an agent to a protein of interest (POI), the method comprising:
    displaying the POI on the surface of the eukaryotic cell according to the method of claim 16,
    contacting the eukaryotic cell with an agent,
    measuring an amount of the agent bound to the cell.

20. The method according to claim 19, wherein the agent is labeled with a directly detectable label.

21. The method of claim 19, wherein the method comprises:
    displaying two or more different proteins of interest (POIs), each displayed on the surface of a different cell,
    contacting the cells displaying said POIs with the agent, and
    measuring an amount of the agent bound to said cells.

22. The method according to claim 21, wherein at least two of the two or more different POIs differ in amino acid sequence by 1 to 20 amino acids.

23. The method according to claim 21, wherein the method comprises a step of generating at least two of the two or more different POIs using a method that includes mutagenesis.

24. The method of claim 19, wherein the method comprises:
    contacting the eukaryotic cell with two or more agents, and
    identifying at least one agent of said two more agents bound to said cell.

25. The kit of claim 13, wherein at least one of the two or more DNA nucleic acids further comprises an insertion site for inserting a nucleotide sequence that encodes a protein of interest (POI), wherein the insertion site is positioned 3' of (i) and 5' of (ii).

26. The kit of claim 13, wherein at least one of the two or more DNA nucleic acids comprises: (iv) a fourth nucleotide sequence that encodes a protein of interest (POI), wherein said first through fourth nucleotide sequences are:
   (a) positioned, from 5' to 3', in the following order: (i), (iv), (ii), (iii); and
   (b) are in frame with one another such that they collectively encode a surface accessible fusion protein comprising the signal polypeptide, the POI, the stalk polypeptide, and the surface anchor polypeptide.

27. The kit of claim 13, wherein at least one of the stalk polypeptides encoded by the two or more DNA nucleic acids comprises a polypeptide sequence having a length of 20 or more amino acids.

28. The kit of claim 13, wherein:
(A) at least one of the signal polypeptides encoded by the two or more DNA nucleic acids:
is a signal polypeptide from a yeast protein;
is from a protein that exhibits post-translational transport to the endoplasmic reticulum (ER); or
comprises an amino acid sequence having 60% or more amino acid sequence identity with the amino acid sequence set forth in any of SEQ ID NOs: 11-17;
(B) at least one of the surface anchor polypeptides encoded by the two or more DNA nucleic acids is a glycosylphosphatidylinositol (GPI) anchor domain;
(C) at least one of the two or more DNA nucleic acids is a recombinant expression vector;
(D) said promoter of at least one of the two or more DNA nucleic acids is functional in a yeast cell; or
(E) any combination thereof.

* * * * *

SEQUENCE LISTING

```
<160> NUMBER OF SEQ ID NOS: 71

<210> SEQ ID NO 1
<211> LENGTH: 258
<212> TYPE: DNA
<213> ORGANISM: Artificial sequence
<220> FEATURE:
<223> OTHER INFORMATION: synthetic sequence

<400> SEQUENCE: 1
atgagattcc catctatctt caccgctgtt ttgttcgctg cttcttctgc tttggctgct      60
ccagctaaca ccaccaccga agacgaaacc gctcaaatcc cagctgaagc tgttatcgac     120
tactctgact tggaaggtga cttcgacgct gctgctttgc cattgtctaa ctctaccaac     180
aacggtttgt cttctaccaa caccaccatc gcttctatcg ctgctaagga agaaggtgtt     240
caattggaca agagagaa                                                    258
```

```
<210> SEQ ID NO 2
<211> LENGTH: 357
<212> TYPE: DNA
<213> ORGANISM: Artificial sequence
<220> FEATURE:
<223> OTHER INFORMATION: synthetic sequence

<400> SEQUENCE: 2
gaggaggagc tgcagattat tcagcctgac aagtccgtgt tggttgcagc tggagagaca    60
gccactctgc gctgcactat tacctctctg tttcctgtgg ggcccatcca gtggttcaga   120
ggagctggac caggccgggt attaatctac aatcaaaggc agggccccct tccccgggta   180
acaactgttt cagacactac aaagagaaac aacatggact tttccatccg catcggtaac   240
atcaccccag cagatgccgg cacctactac tgtattaagt tccggaaagg gagccccgat   300
gacgtggagt ttaagtctgg agcaggcact gagctgtctg tgcgcgccaa accctct      357

<210> SEQ ID NO 3
<211> LENGTH: 27
<212> TYPE: DNA
<213> ORGANISM: Artificial sequence
<220> FEATURE:
<223> OTHER INFORMATION: synthetic sequence

<400> SEQUENCE: 3
tacccatacg atgttccaga ttacgct                                         27

<210> SEQ ID NO 4
<211> LENGTH: 1947
<212> TYPE: DNA
<213> ORGANISM: Artificial sequence
<220> FEATURE:
<223> OTHER INFORMATION: synthetic sequence

<400> SEQUENCE: 4
caaacatcct caccctctac agaagcatca gtatcaacct ctagtacctc ttcctctgct    60
tcacaatcat ctgacccaac tacaacatct tcgtccagtt catcgtcttc cccatcttcc   120
caatctgagg aaatttcatc atcaccgacg gtctcaacta caccatcaac ttcttcatca   180
tcttcctcaa tgacttcaac caccacaaca agtcaatctt caacttccac tacaagttca   240
gctccagtta cagatgtgac agtttcctca tcgcctagta aatctacctc tacttcgaca   300
agtacagaaa catctaaaac acctacttca atgacagagt atacatctag tacatcgata   360
atttcgactc cagttagtca ctcgcagaca ggtttgtcgg cttcatcaag ttcatcatct   420
acaacatccg ttcttcgtc cactaaatca gaaagttcga caacatctgg ctcttcccag   480
tccgtggaat caacctccag ccacgccact gttcttgcta attccgcaga aatggtcaca   540
acatcctcta gttcatcctc aacatccgaa atgtcattaa ctagtactgc taccagtgta   600
ccagtctcat ctagtagcag tacgacatat tctactagcg catctacaca agccgtcact   660
acaacatctt cttccactgt atctacaact tcttctagta caacgttaac aagcgcattc   720
acacattctt caaccacatc gtccgaccag ccacccagcg cactacaag tccatctacg   780 acacacgaac tcatgtaac cactcagacg tcatcagaaa catcttcttc taagtcatct   840
tctacttctt cttcaagtac atctcaaacc tctgagtctg caacaccatc cgattccgta   900
tcacctggaa gttctacatc aacatcttct agtagcactt ctacttccac ttctatttcc   960
agtggagaaa cgacaacttc ttcttcttca tcatctgcca cgaccacttc taacagcgca  1020
accttgtcag tctctaccac acaaaacttcg attgaagcca gttcatctac tacatctaca  1080
```

```
tctagttcaa caattacaac ttcaagtagt agcgctcaca tatcgtcgaa atctcaatct    1140
agtattacct atccctcttc ctcgacatct tcatctacat cgtcctcaat ttctagcgaa    1200
tctgaaagtt ttgaatcgac atcagcagaa gatgctccat caacagcacc ttcatcaagt    1260
gtctcttcta agagttctac ctctacaaca tcaagcacat cgacatcttc aagcactcca    1320
tctccatcac catcttccgt gagttcttcc tccaccagct cattgacaac ttctgctgta    1380
tcaacaccag ctacctctca ttctcaaagt actgtagtaa ccaccactac tattactaca    1440
tcaacaggtc cagtgatgtc tacgacaaca gcttattctt ctagttctac tagcagctcg    1500
gaatcttctg aggttcagtc tgtcatgtca tctacgccta gttcaacatc aacaacaacc    1560
agttcggaat ctacttcatc tagctccaca gcttctacct caccatcaac ctcgcaaact    1620
ttcgaaactt ctcctactat aggaggtgtc ccctcaacca cttcatttgt ctctacgcca    1680
acaacgaaat tgtcgcacac tacttccact atgacagcac agtccgatag taagtctacc    1740
cactcctcaa gcacatcgac agaagataaa tcatccactg cttctgcagt tgacgaaagc    1800
actacaacat ccacttccac ggagtctact acatcagtaa catcaggcac ctcccattcc    1860
gctaaagaat cttcgtcaaa ttctaaggtg tatagttcac agacagcaca ctcatccata    1920
agtgttgcat catcacctag tacaaag                                        1947

<210> SEQ ID NO 5
<211> LENGTH: 111
<212> TYPE: DNA
<213> ORGANISM: Artificial sequence
<220> FEATURE:
<223> OTHER INFORMATION: synthetic sequence

<400> SEQUENCE: 5
caaatccaat cttctatggt tgaaatctct acctacgctg gttctgctaa ctctgttaac     60
gctggtgctg gtgctggtgc tttgttcttg ttgttgtctt tggctatcat c             111

<210> SEQ ID NO 6
<211> LENGTH: 8584
<212> TYPE: DNA
<213> ORGANISM: Artificial sequence
<220> FEATURE:
<223> OTHER INFORMATION: synthetic sequence

<400> SEQUENCE: 6
ggtacccgac aggttatcag caacaacaca gtcatatcca ttctcaatta gctctaccac     60
agtgtgtgaa ccaatgtatc cagcaccacc tgtaaccaaa acaattttag aagtactttc    120
actttgtaac tgagctgtca tttatattga attttcaaaa attcttactt tttttttgga    180
tggacgcaaa gaagtttaat aatcatatta catggcatta ccaccatata catatccata    240
tacatatcca tatctaatct tacttatatg ttgtggaaat gtaaagagcc ccattatctt    300
agcctaaaaa aaccttctct ttggaacttt cagtaatacg cttaactgct cattgctata    360
ttgaagtacg gattagaagc cgccgagcgg gtgacagccc tccgaaggaa gactctcctc    420
cgtgcgtcct cgtcttcacc ggtcgcgttc ctgaaacgca gatgtgcctc gcgccgcact    480
gctccgaaca ataaagattc tacaatacta gcttttatgg ttatgaagag gaaaaattgg    540
cagtaacctg gccccacaaa ccttcaaatg aacgaatcaa attaacaacc ataggatgat    600
aatgcgatta gttttttagc cttatttctg gggtaattaa tcagcgaagc gatgattttt    660
gatctattaa cagatatata aatgcaaaaa ctgcataacc actttaacta atactttcaa    720 catttttcggt ttgtattact tcttattcaa atgtaataaa agtatcaaca aaaaattgtt    780
```

-continued

| | |
|---|---|
| aatatacctc tatactttaa cgtcaaggag aaaaaacccc ggatcgaatt caaccctcac | 840 |
| taaagggcgg ccgccatgag attcccatct atcttcaccg ctgttttgtt cgctgcttct | 900 |
| tctgctttgg ctgctccagc taacaccacc accgaagacg aaaccgctca atcccagct | 960 |
| gaagctgtta tcgactactc tgacttggaa ggtgacttcg acgctgctgc tttgccattg | 1020 |
| tctaactcta ccaacaacgg tttgtcttct accaacacca ccatcgcttc tatcgctgct | 1080 |
| aaggaagaag gtgttcaatt ggacaagaga gaagctagcg cagaggagga gctgcagatt | 1140 |
| attcagcctg acaagtccgt gttggttgca gctggagaga cagccactct gcgctgcact | 1200 |
| attacctctc tgtttcctgt ggggcccatc cagtggttca gaggagctgg accaggccgg | 1260 |
| gtattaatct acaatcaaag gcagggcccc ttccccgggt aacaactgt ttcagacact | 1320 |
| acaaagagaa acaacatgga cttttccatc cgcatcggta acatcacccc agcagatgcc | 1380 |
| ggcacctact actgtattaa gttccggaaa gggagccccg atgacgtgga gtttaagtct | 1440 |
| ggagcaggca ctgagctgtc tgtgcgcgcc aaaccctctg gatcctaccc atacgatgtt | 1500 |
| ccagattacg ctcaaacatc ctcaccctct acagaagcat cagtatcaac ctctagtacc | 1560 |
| tcttcctctg cttcacaatc atctgaccca actacaacat cttcgtccag ttcatcgtct | 1620 |
| tccccatctt cccaatctga ggaaatttca tcatcaccga cggtctcaac tacaccatca | 1680 |
| acttcttcat catcttcctc aatgacttca accaccacaa caaagtcaat ctcaacttcc | 1740 |
| actacaagtt cagctccagt tacagatgtg acagtttcct catcgcctag taaatctacc | 1800 |
| tctacttcga caagtacaga acatctaaa acacctactt caatgacaga gtatacatct | 1860 |
| agtacatcga taatttcgac tccagttagt cactcgcaga caggtttgtc ggcttcatca | 1920 |
| agttcatcat ctacaacatc cggttcttcg tccactaaat cagaaagttc gacaacatct | 1980 |
| ggctcttccc agtccgtgga atcaacctcc agccacgcca ctgttcttgc taattccgca | 2040 |
| gaaatggtca caacatcctc tagttcatcc tcaacatccg aaatgtcatt aactagtact | 2100 |
| gctaccagtg taccagtctc atctagtagc agtacgacat attctactag cgcatctaca | 2160 |
| caagccgtca ctacaacatc ttcttccact gtatctacaa cttcttctag tacaacgtta | 2220 |
| acaagcgcat tcacacattc ttcaaccaca tcgtccgacc agccacccag cgacactaca | 2280 |
| agtccatcta cgacacacga acctcatgta accactcaga cgtcatcaga acatcttct | 2340 |
| tctaagtcat cttctacttc ttcttcaagt acatctcaaa cctctgagtc tgcaacacca | 2400 |
| tccgattccg tatcacctgg aagttctaca tcaacatctt ctagtagcac ttctacttcc | 2460 |
| acttctattt ccagtggaga aacgacaact tcttcttctt catcatctgc cacgaccact | 2520 |
| tctaacagcg caaccttgtc agtctctacc acacaaactt cgattgaagc cagttcatct | 2580 |
| actacatcta catctagttc aacaattaca acttcaagta gtagcgctca catatcgtcg | 2640 |
| aaatctcaat ctagtattac ctatccctct tcctcgacat cttcatctac atcgtcctca | 2700 |
| atttctagcg aatctgaaag ttttgaatcg acatcagcag aagatgctcc atcaacagca | 2760 |
| ccttcatcaa gtgtctcttc taagagttct acctctacaa catcaagcac atcgacatct | 2820 |
| tcaagcactc catctccatc accatcttcc gtgagttctt cctccaccag ctcattgaca | 2880 |
| acttctgctg tatcaacacc agctacctct cattctcaaa gtactgtagt aaccaccact | 2940 |
| actattacta catcaacagg tccagtgatg tctacgacaa cagcttattc ttctagttct | 3000 |
| actagcagct cggaatcttc tgaggttcag tctgtcatgt catctacgcc tagttcaaca | 3060 |
| tcaacaacaa ccagttcgga atctacttca tctagctcca cagcttctac ctcaccatca | 3120 |
| acctcgcaaa cttccgaaac ttctcctact ataggaggtg tcccctcaac cacttcattt | 3180 |

```
gtctctacgc caacaacgaa attgtcgcac actacttcca ctatgacagc acagtccgat    3240
agtaagtcta cccactcctc aagcacatcg acagaagata aatcatccac tgcttctgca    3300
gttgacgaaa gcactacaac atccacttcc acggagtcta ctacatcagt aacatcaggc    3360
acctcccatt ccgctaaaga atcttcgtca aattctaagg tgtatagttc acagacagca    3420
cactcatcca taagtgttgc atcatcacct agtacaaagg gcgcccaaat ccaatcttct    3480
atggttgaaa tctctaccta cgctggttct gctaactctg ttaacgctgg tgctggtgct    3540
ggtgctttgt tcttgttgtt gtctttggct atcatctaat gattaattaa ctcgagatct    3600
gataacaaca gtgtagatgt aacaaaatcg actttgttcc cactgtactt ttagctcgta    3660
caaaatacaa tatactttc atttctccgt aaacaacatg ttttcccatg taatatcctt    3720
ttctattttt cgttccgtta ccaactttac acatacttta tatagctatt cacttctata    3780
cactaaaaaa ctaagacaat tttaattttg ctgcctgcca tatttcaatt tgttataaat    3840
tcctataatt tatcctatta gtagctaaaa aaagatgaat gtgaatcgaa tcctaagaga    3900
attgagctcc aattcgccct atagtgagtc gtattacaat tcactggccg tcgttttaca    3960
acgtcgtgac tgggaaaacc ctggcgttac ccaacttaat cgccttgcag cacatccccc    4020
cttcgccagc tggcgtaata gcgaagaggc ccgcaccgat cgcccttccc aacagttgcg    4080
cagcctgaat ggcgaatggc gcgacgcgcc ctgtagcggc gcattaagcg cggcgggtgt    4140
ggtggttacg cgcagcgtga ccgctacact tgccagcgcc ctagcgcccg ctcctttcgc    4200
tttcttccct tcctttctcg ccacgttcgc cggctttccc cgtcaagctc taaatcgggg    4260
gctcccttta gggttccgat ttagtgcttt acggcacctc gaccccaaaa aacttgatta    4320
gggtgatggt tcacgtagtg gccatcgcc ctgatagacg ttttcgcc ctttgacgtt    4380 ggagtccacg ttctttaata gtggactctt gttccaaact ggaacaacac tcaaccctat    4440
ctcggtctat tcttttgatt tataagggat tttgccgatt tcggcctatt ggttaaaaaa    4500
tgagctgatt taacaaaaat ttaacgcgaa ttttaacaaa atattaacgt ttacaatttc    4560
ctgatgcggt attttctcct tacgcatctg tgcggtattt cacaccgcag gcaagtgcac    4620
aaacaatact taaataaata ctactcagta ataacctatt tcttagcatt tttgacgaaa    4680
tttgctattt tgttagagtc ttttacacca tttgtctcca cacctccgct tacatcaaca    4740
ccaataacgc catttaatct aagcgcatca ccaacatttt ctggcgtcag tccaccagct    4800
aacataaaat gtaagctttc ggggctctct tgccttccaa cccagtcaga aatcgagttc    4860
caatccaaaa gttcacctgt cccacctgct tctgaatcaa acaagggaat aaacgaatga    4920
ggtttctgtg aagctgcact gagtagtatg ttgcagtctt ttggaaatac gagtctttta    4980
ataactggca aaccgaggaa ctcttggtat tcttgccacg actcatctcc atgcagttgg    5040
acgatatcaa tgccgtaatc attgaccaga gccaaaacat cctccttagg ttgattacga    5100
aacacgccaa ccaagtattt cggagtgcct gaactatttt tatatgcttt tacaagactt    5160 gaaatttcc ttgcaataac cgggtcaatt gttctctttc tattgggcac acatataata    5220
cccagcaagt cagcatcgga atctagagca cattctgcgg cctctgtgct ctgcaagccg    5280
caaactttca ccaatggacc agaactacct gtgaaattaa taacagacat actccaagct    5340
gcctttgtgt gcttaatcac gtatactcac gtgctcaata gtcaccaatg ccctccctct    5400
tggccctctc cttttctttt ttcgaccgaa ttaattctta atcggcaaaa aaagaaaagc    5460
tccggatcaa gattgtacgt aaggtgacaa gctatttttc aataaagaat atcttccact    5520
actgccatct ggcgtcataa ctgcaaagta cacatatatt acgatgctgt ctattaaatg    5580
```

```
cttcctatat tatatatata gtaatgtcgt ttatggtgca ctctcagtac aatctgctct    5640
gatgccgcat agttaagcca gccccgacac ccgccaacac ccgctgacgc gccctgacgg    5700
gcttgtctgc tcccggcatc cgcttacaga caagctgtga ccgtctccgg gagctgcatg    5760
tgtcagaggt tttcaccgtc atcaccgaaa cgcgcgagac gaaagggcct cgtgatacgc    5820 ctattttat aggttaatgt catgataata atggtttctt aggacggatc gcttgcctgt     5880
aacttacacg cgcctcgtat cttttaatga tggaataatt tgggaattta ctctgtgttt    5940 atttatttt atgttttgta tttggatttt agaaagtaaa taagaaggt agaagagtta      6000 cggaatgaag aaaaaaaaat aaacaaaggt ttaaaaaatt tcaacaaaaa gcgtactttta   6060 catatatatt tattagacaa gaaaagcaga ttaaatagat atacattcga ttaacgataa    6120
gtaaaatgta aaatcacagg attttcgtgt gtggtcttct acacagacaa gatgaaacaa    6180
ttcggcatta atacctgaga gcaggaagag caagataaaa ggtagtattt gttggcgatc    6240
cccctagagt cttttacatc ttcggaaaac aaaaactatt ttttctttaa tttctttttt    6300
tactttctat ttttaatta tatatttata ttaaaaaatt taaattataa ttattttat     6360 agcacgtgat gaaaggacc caggtggcac ttttcgggga aatgtgcgcg gaaccccctat    6420 ttgtttattt ttctaaatac attcaaatat gtatccgctc atgagacaat aaccctgata    6480
aatgcttcaa taatattgaa aaaggaagag tatgagtatt caacatttcc gtgtcgccct    6540
tattcccttt tttgcggcat tttgccttcc tgtttttgct cacccagaaa cgctggtgaa    6600
agtaaaagat gctgaagatc agttgggtgc acgagtgggt tacatcgaac tggatctcaa    6660
cagcggtaag atccttgaga gttttcgccc cgaagaacgt tttccaatga tgagcacttt    6720
taaagttctg ctatgtggcg cggtattatc ccgtattgac gccgggcaag agcaactcgg    6780
tcgccgcata cactattctc agaatgactt ggttgagtac tcaccagtca cagaaaagca    6840
tcttacggat ggcatgacag taagagaatt atgcagtgct gccataacca tgagtgataa    6900
cactgcggcc aacttacttc tgacaacgat cggaggaccg aaggagctaa ccgcttttt     6960 tcacaacatg gggatcatg taactcgcct tgatcgttgg gaaccggagc tgaatgaagc     7020
cataccaaac gacgagcgtg acaccacgat gcctgtagca atggcaacaa cgttgcgcaa    7080
actattaact ggcgaactac ttactctagc ttcccggcaa caattaatag actggatgga    7140
ggcggataaa gttgcaggac cacttctgcg ctcggccctt ccggctggct ggtttattgc    7200
tgataaatct ggagccggtg agcgtgggtc tcgcggtatc attgcagcac tggggccaga    7260
tggtaagccc tcccgtatcg tagttatcta cacgacgggc agtcaggcaa ctatggatga    7320
acgaaataga cagatcgctg agataggtgc ctcactgatt aagcattggt aactgtcaga    7380
ccaagtttac tcatatatac tttagattga tttaaaactt cattttaat ttaaaaggat    7440 ctaggtgaag atcctttttg ataatctcat gaccaaaatc ccttaacgtg agttttcgtt    7500
ccactgagcg tcagacccg tagaaaagat caaaggatct tcttgagatc cttttttct    7560 gcgcgtaatc tgctgcttgc aaacaaaaaa accaccgcta ccagcggtgg tttgtttgcc    7620
ggatcaagag ctaccaactc tttttccgaa ggtaactggc ttcagcagag cgcagatacc    7680
aaatactgtc cttctagtgt agccgtagtt aggccaccac ttcaagaact ctgtagcacc    7740
gcctacatac ctcgctctgc taatcctgtt accagtggct gctgccagtg gcgataagtc    7800
gtgtcttacc gggttggact caagacgata gttaccggat aaggcgcagc ggtcgggctg    7860
aacggggggt tcgtgcacac agcccagctt ggagcgaacg acctacaccg aactgagata    7920
```

```
cctacagcgt gagcattgag aaagcgccac gcttcccgaa gggagaaagg cggacaggta   7980
tccggtaagc ggcagggtcg gaacaggaga gcgcacgagg gagcttccag ggggaacgc    8040 ctggtatctt tatagtcctg tcgggtttcg ccacctctga cttgagcgtc gattttgtg    8100 atgctcgtca gggggccga gcctatggaa aaacgccagc aacgcggcct ttttacggtt    8160
cctggccttt tgctggcctt tgctcacat gttctttcct gcgttatccc ctgattctgt    8220
ggataaccgt attaccgcct ttgagtgagc tgataccgct cgccgcagcc gaacgaccga   8280
gcgcagcgag tcagtgagcg aggaagcgga agagcgccca atacgcaaac cgcctctccc   8340
cgcgcgttgg ccgattcatt aatgcagctg gcacgacagg tttcccgact ggaaagcggg   8400
cagtgagcgc aacgcaatta atgtgagtta cctcactcat taggcacccc aggctttaca   8460
ctttatgctt ccggctccta tgttgtgtgg aattgtgagc ggataacaat ttcacacagg   8520
aaacagctat gaccatgatt acgccaagct cggaattaac cctcactaaa gggaacaaaa   8580
gctg                                                                8584
```

```
<210> SEQ ID NO 7
<211> LENGTH: 119
<212> TYPE: PRT
<213> ORGANISM: Artificial sequence
<220> FEATURE:
<223> OTHER INFORMATION: synthetic sequence

<400> SEQUENCE: 7

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

```
<210> SEQ ID NO 8
<211> LENGTH: 9
<212> TYPE: PRT
<213> ORGANISM: Artificial sequence
<220> FEATURE:
<223> OTHER INFORMATION: synthetic sequence

<400> SEQUENCE: 8

Tyr Pro Tyr Asp Val Pro Asp Tyr Ala
1               5
```

```
<210> SEQ ID NO 9
<211> LENGTH: 907
<212> TYPE: PRT
<213> ORGANISM: Artificial sequence
<220> FEATURE:
<223> OTHER INFORMATION: synthetic sequence
```

<400> SEQUENCE: 9

```
Met Arg Phe Pro Ser Ile Phe Thr Ala Val Leu Phe Ala Ala Ser Ser
1               5                   10                  15

Ala Leu Ala Ala Pro Ala Asn Thr Thr Thr Glu Asp Glu Thr Ala Gln
            20                  25                  30

Ile Pro Ala Glu Ala Val Ile Asp Tyr Ser Asp Leu Glu Gly Asp Phe
        35                  40                  45

Asp Ala Ala Ala Leu Pro Leu Ser Asn Ser Thr Asn Asn Gly Leu Ser
    50                  55                  60

Ser Thr Asn Thr Thr Ile Ala Ser Ile Ala Ala Lys Glu Glu Gly Val
65                  70                  75                  80

Gln Leu Asp Lys Arg Glu Ala Ser Ala Glu Glu Leu Gln Ile Ile
                85                  90                  95

Gln Pro Asp Lys Ser Val Leu Val Ala Ala Gly Glu Thr Ala Thr Leu
            100                 105                 110

Arg Cys Thr Ile Thr Ser Leu Phe Pro Val Gly Pro Ile Gln Trp Phe
        115                 120                 125

Arg Gly Ala Gly Pro Gly Arg Val Leu Ile Tyr Asn Gln Arg Gln Gly
    130                 135                 140

Pro Phe Pro Arg Val Thr Val Ser Asp Thr Thr Lys Arg Asn Asn
145                 150                 155                 160

Met Asp Phe Ser Ile Arg Ile Gly Asn Ile Thr Pro Ala Asp Ala Gly
                165                 170                 175

Thr Tyr Tyr Cys Ile Lys Phe Arg Lys Gly Ser Pro Asp Asp Val Glu
            180                 185                 190

Phe Lys Ser Gly Ala Gly Thr Glu Leu Ser Val Arg Ala Lys Pro Ser
        195                 200                 205

Gly Ser Tyr Pro Tyr Asp Val Pro Asp Tyr Ala Gln Thr Ser Ser Pro
    210                 215                 220

Ser Thr Glu Ala Ser Val Ser Thr Ser Ser Thr Ser Ser Ser Ala Ser
225                 230                 235                 240

Gln Ser Ser Asp Pro Thr Thr Ser Ser Ser Ser Ser Ser Ser Ser
                245                 250                 255

Pro Ser Ser Gln Ser Glu Glu Ile Ser Ser Pro Thr Val Ser Thr
            260                 265                 270

Thr Pro Ser Thr Ser Ser Ser Ser Ser Met Thr Ser Thr Thr Thr
        275                 280                 285

Thr Lys Ser Ile Ser Thr Ser Thr Ser Ser Ala Pro Val Thr Asp
    290                 295                 300

Val Thr Val Ser Ser Ser Pro Ser Lys Ser Thr Ser Thr Ser Thr Ser
305                 310                 315                 320

Thr Glu Thr Ser Lys Thr Pro Thr Ser Met Thr Glu Tyr Thr Ser Ser
                325                 330                 335

Thr Ser Ile Ile Ser Thr Pro Val Ser His Ser Gln Thr Gly Leu Ser
            340                 345                 350

Ala Ser Ser Ser Ser Ser Ser Thr Thr Ser Gly Ser Ser Thr Lys
        355                 360                 365

Ser Glu Ser Ser Thr Thr Ser Gly Ser Ser Gln Ser Val Glu Ser Thr
    370                 375                 380

Ser Ser His Ala Thr Val Leu Ala Asn Ser Ala Glu Met Val Thr Thr
385                 390                 395                 400

Ser Ser Ser Ser Ser Ser Thr Ser Glu Met Ser Leu Thr Ser Thr Ala
                405                 410                 415
```

```
Thr Ser Val Pro Val Ser Ser Ser Ser Thr Thr Tyr Ser Thr Ser
            420                 425                 430

Ala Ser Thr Gln Ala Val Thr Thr Thr Ser Ser Ser Thr Val Ser Thr
                435                 440                 445

Thr Ser Ser Ser Thr Thr Leu Thr Ser Ala Phe Thr His Ser Ser Thr
450                         455                 460

Thr Ser Ser Asp Gln Pro Pro Ser Asp Thr Thr Ser Pro Ser Thr Thr
465                 470                 475                 480

His Glu Pro His Val Thr Thr Gln Thr Ser Glu Thr Ser Ser Ser
                485                 490                 495

Lys Ser Ser Ser Thr Ser Ser Ser Thr Ser Gln Thr Ser Glu Ser
            500                 505                 510

Ala Thr Pro Ser Asp Ser Val Ser Pro Gly Ser Ser Thr Ser Thr Ser
            515                 520                 525

Ser Ser Ser Thr Ser Thr Ser Thr Ser Ile Ser Ser Gly Glu Thr Thr
            530                 535                 540

Thr Ser Ser Ser Ser Ser Ser Ala Thr Thr Thr Ser Asn Ser Ala Thr
545                 550                 555                 560

Leu Ser Val Ser Thr Thr Gln Thr Ser Ile Glu Ala Ser Ser Ser Thr
                565                 570                 575

Thr Ser Thr Ser Ser Ser Thr Ile Thr Thr Ser Ser Ser Ala His
            580                 585                 590

Ile Ser Ser Lys Ser Gln Ser Ser Ile Thr Tyr Pro Ser Ser Ser Thr
            595                 600                 605

Ser Ser Ser Thr Ser Ser Ser Ile Ser Ser Glu Ser Glu Ser Phe Glu
    610                 615                 620

Ser Thr Ser Ala Glu Asp Ala Pro Ser Thr Ala Pro Ser Ser Ser Val
625                 630                 635                 640

Ser Ser Lys Ser Ser Thr Ser Thr Thr Ser Ser Thr Ser Thr Ser Ser
            645                 650                 655

Ser Thr Pro Ser Pro Ser Pro Ser Ser Val Ser Ser Ser Ser Thr Ser
            660                 665                 670

Ser Leu Thr Thr Ser Ala Val Ser Thr Pro Ala Thr Ser His Ser Gln
    675                 680                 685

Ser Thr Val Val Thr Thr Thr Thr Ile Thr Thr Ser Thr Gly Pro Val
    690                 695                 700

Met Ser Thr Thr Thr Ala Tyr Ser Ser Ser Thr Ser Ser Ser Glu
705                 710                 715                 720

Ser Ser Glu Val Gln Ser Val Met Ser Ser Thr Pro Ser Ser Thr Ser
                725                 730                 735

Thr Thr Thr Ser Ser Glu Ser Thr Ser Ser Ser Ser Thr Ala Ser Thr
            740                 745                 750

Ser Pro Ser Thr Ser Gln Thr Phe Glu Thr Ser Pro Thr Ile Gly Gly
            755                 760                 765

Val Pro Ser Thr Thr Ser Phe Val Ser Thr Pro Thr Thr Lys Leu Ser
    770                 775                 780

His Thr Thr Ser Thr Met Thr Ala Gln Ser Asp Ser Lys Ser Thr His
785                 790                 795                 800

Ser Ser Ser Thr Ser Thr Glu Asp Lys Ser Ser Thr Ala Ser Ala Val
            805                 810                 815

Asp Glu Ser Thr Thr Thr Ser Thr Ser Thr Glu Ser Thr Thr Ser Val
            820                 825                 830
```

Thr Ser Gly Thr Ser His Ser Ala Lys Glu Ser Ser Asn Ser Lys
            835                 840                 845

Val Tyr Ser Ser Gln Thr Ala His Ser Ser Ile Ser Val Ala Ser Ser
850                 855                 860

Pro Ser Thr Lys Gly Ala Gln Ile Gln Ser Ser Met Val Glu Ile Ser
865                 870                 875                 880

Thr Tyr Ala Gly Ser Ala Asn Ser Val Asn Ala Gly Ala Gly Ala Gly
                885                 890                 895

Ala Leu Phe Leu Leu Leu Ser Leu Ala Ile Ile
            900                 905

<210> SEQ ID NO 10
<211> LENGTH: 910
<212> TYPE: PRT
<213> ORGANISM: Artificial sequence
<220> FEATURE:
<223> OTHER INFORMATION: synthetic sequence

<400> SEQUENCE: 10

Met Arg Phe Pro Ser Ile Phe Thr Ala Val Leu Phe Ala Ala Ser Ser
1               5                   10                  15

Ala Leu Ala Ala Pro Ala Asn Thr Thr Thr Glu Asp Glu Thr Ala Gln
            20                  25                  30

Ile Pro Ala Glu Ala Val Ile Asp Tyr Ser Asp Leu Glu Gly Asp Phe
        35                  40                  45

Asp Ala Ala Ala Leu Pro Leu Ser Asn Ser Thr Asn Asn Gly Leu Ser
    50                  55                  60

Ser Thr Asn Thr Thr Ile Ala Ser Ile Ala Ala Lys Glu Glu Gly Val
65                  70                  75                  80

Gln Leu Asp Lys Arg Glu Ala Ser Ala Glu Glu Glu Leu Gln Ile Ile
            85                  90                  95

Gln Pro Asp Lys Ser Val Leu Val Ala Ala Gly Glu Thr Ala Thr Leu
        100                 105                 110

Arg Cys Thr Ile Thr Ser Leu Phe Pro Val Gly Pro Ile Gln Trp Phe
    115                 120                 125

Arg Gly Ala Gly Pro Gly Arg Val Leu Ile Tyr Asn Gln Arg Gln Gly
130                 135                 140

Pro Phe Pro Arg Val Thr Thr Val Ser Asp Thr Thr Lys Arg Asn Asn
145                 150                 155                 160

Met Asp Phe Ser Ile Arg Ile Gly Asn Ile Thr Pro Ala Asp Ala Gly
            165                 170                 175

Thr Tyr Tyr Cys Ile Lys Phe Arg Lys Gly Ser Pro Asp Asp Val Glu
        180                 185                 190

Phe Lys Ser Gly Ala Gly Thr Glu Leu Ser Val Arg Ala Lys Pro Ser
    195                 200                 205

Gly Ser Tyr Pro Tyr Asp Val Pro Asp Tyr Ala Gln Thr Ser Ser Pro
210                 215                 220

Ser Thr Glu Ala Ser Val Ser Thr Ser Ser Thr Ser Ser Ser Ala Ser
225                 230                 235                 240

Gln Ser Ser Asp Pro Thr Thr Thr Ser Ser Ser Ser Ser Ser Ser Ser
            245                 250                 255

Pro Ser Ser Gln Ser Glu Glu Ile Ser Ser Ser Pro Thr Val Ser Thr
        260                 265                 270

Thr Pro Ser Thr Ser Ser Ser Ser Ser Ser Met Thr Ser Thr Thr Thr
    275                 280                 285

```
Thr Lys Ser Ile Ser Thr Ser Thr Ser Ser Ala Pro Val Thr Asp
    290             295             300
Val Thr Val Ser Ser Pro Ser Lys Ser Thr Ser Thr Ser Thr Ser
305             310             315             320
Thr Glu Thr Ser Lys Thr Pro Thr Ser Met Thr Glu Tyr Thr Ser Ser
            325             330             335
Thr Ser Ile Ile Ser Thr Pro Val Ser His Ser Gln Thr Gly Leu Ser
            340             345             350
Ala Ser Ser Ser Ser Ser Thr Ser Gly Ser Ser Ser Thr Lys
        355             360             365
Ser Glu Ser Ser Thr Thr Ser Gly Ser Ser Gln Ser Val Glu Ser Thr
    370             375             380
Ser Ser His Ala Thr Val Leu Ala Asn Ser Ala Glu Met Val Thr Thr
385             390             395             400
Ser Ser Ser Ser Ser Ser Thr Ser Glu Met Ser Leu Thr Ser Thr Ala
                405             410             415
Thr Ser Val Pro Val Ser Ser Ser Ser Thr Thr Tyr Ser Thr Ser
            420             425             430
Ala Ser Thr Gln Ala Val Thr Thr Thr Ser Ser Ser Thr Val Ser Thr
            435             440             445
Thr Ser Ser Ser Thr Thr Leu Thr Ser Ala Phe Thr His Ser Ser Thr
450             455             460
Thr Ser Ser Asp Gln Pro Pro Ser Asp Thr Thr Ser Pro Ser Thr Thr
465             470             475             480
His Glu Pro His Val Thr Thr Gln Thr Ser Ser Glu Thr Ser Ser Ser
            485             490             495
Lys Ser Ser Ser Thr Ser Ser Ser Thr Ser Gln Thr Ser Glu Ser
        500             505             510
Ala Thr Pro Ser Asp Ser Val Ser Pro Gly Ser Ser Thr Ser Thr Ser
    515             520             525
Ser Ser Ser Thr Ser Thr Ser Thr Ser Ile Ser Ser Gly Glu Thr Thr
    530             535             540
Thr Ser Ser Ser Ser Ser Ser Ala Thr Thr Thr Ser Asn Ser Ala Thr
545             550             555             560
Leu Ser Val Ser Thr Thr Gln Thr Ser Ile Glu Ala Ser Ser Ser Thr
            565             570             575
Thr Ser Thr Ser Ser Ser Thr Ile Thr Thr Ser Ser Ser Ala His
            580             585             590
Ile Ser Ser Lys Ser Gln Ser Ser Ile Thr Tyr Pro Ser Ser Ser Thr
    595             600             605
Ser Ser Ser Thr Ser Ser Ser Ile Ser Ser Glu Ser Glu Ser Phe Glu
    610             615             620
Ser Thr Ser Ala Glu Asp Ala Pro Ser Thr Ala Pro Ser Ser Ser Val
625             630             635             640
Ser Ser Lys Ser Ser Thr Ser Thr Ser Ser Thr Ser Thr Ser Ser
            645             650             655
Ser Thr Pro Ser Pro Ser Pro Ser Ser Val Ser Ser Ser Ser Thr Ser
            660             665             670
Ser Leu Thr Thr Ser Ala Val Ser Thr Pro Ala Thr Ser His Ser Gln
    675             680             685
Ser Thr Val Val Thr Thr Thr Thr Ile Thr Thr Ser Thr Gly Pro Val
    690             695             700
```

```
Met Ser Thr Thr Thr Ala Tyr Ser Ser Ser Thr Ser Ser Ser Glu
705                 710                 715                 720

Ser Ser Glu Val Gln Ser Val Met Ser Ser Thr Pro Ser Ser Thr Ser
            725                 730                 735

Thr Thr Thr Ser Ser Glu Ser Thr Ser Ser Ser Thr Ala Ser Thr
            740                 745                 750

Ser Pro Ser Thr Ser Gln Thr Phe Glu Thr Ser Pro Thr Ile Gly Gly
            755                 760                 765

Val Pro Ser Thr Thr Ser Phe Val Ser Thr Pro Thr Thr Lys Leu Ser
        770                 775                 780

His Thr Thr Ser Thr Met Thr Ala Gln Ser Asp Ser Lys Ser Thr His
785                 790                 795                 800

Ser Ser Ser Thr Ser Thr Glu Asp Lys Ser Ser Thr Ala Ser Ala Val
                805                 810                 815

Asp Glu Ser Thr Thr Thr Ser Thr Ser Thr Glu Ser Thr Thr Ser Val
                820                 825                 830

Thr Ser Gly Thr Ser His Ser Ala Lys Glu Ser Ser Ser Asn Ser Lys
            835                 840                 845

Val Tyr Ser Ser Gln Thr Ala His Ser Ser Ile Ser Val Ala Ser Ser
        850                 855                 860

Pro Ser Thr Lys Gly Ala Ile Gln Gln Asn Phe Thr Ser Thr Ser Leu
865                 870                 875                 880

Met Ile Ser Thr Tyr Glu Gly Lys Ala Ser Ile Phe Phe Ser Ala Glu
                885                 890                 895

Leu Gly Ser Ile Ile Phe Leu Leu Leu Ser Tyr Leu Leu Phe
            900                 905                 910

<210> SEQ ID NO 11
<211> LENGTH: 87
<212> TYPE: PRT
<213> ORGANISM: Artificial sequence
<220> FEATURE:
<223> OTHER INFORMATION: synthetic sequence

<400> SEQUENCE: 11

Met Arg Phe Pro Ser Ile Phe Thr Ala Val Leu Phe Ala Ala Ser Ser
1               5                   10                  15

Ala Leu Ala Ala Pro Ala Asn Thr Thr Thr Glu Asp Glu Thr Ala Gln
            20                  25                  30

Ile Pro Ala Glu Ala Val Ile Asp Tyr Ser Asp Leu Glu Gly Asp Phe
        35                  40                  45

Asp Ala Ala Leu Pro Leu Ser Asn Ser Thr Asn Asn Gly Leu Ser
    50                  55                  60

Ser Thr Asn Thr Thr Ile Ala Ser Ile Ala Ala Lys Glu Glu Gly Val
65                  70                  75                  80

Gln Leu Asp Lys Arg Glu Ala
            85

<210> SEQ ID NO 12
<211> LENGTH: 20
<212> TYPE: PRT
<213> ORGANISM: Artificial sequence
<220> FEATURE:
<223> OTHER INFORMATION: synthetic sequence
```

```
<400> SEQUENCE: 12

Met Arg Phe Pro Ser Ile Phe Thr Ala Val Leu Phe Ala Ala Ser Ser
1               5                   10                  15

Ala Leu Ala Ala
            20

<210> SEQ ID NO 13
<211> LENGTH: 19
<212> TYPE: PRT
<213> ORGANISM: Artificial sequence
<220> FEATURE:
<223> OTHER INFORMATION: synthetic sequence

<400> SEQUENCE: 13

Met Gln Leu Leu Arg Cys Phe Ser Ile Phe Ser Val Ile Ala Ser Val
1               5                   10                  15

Leu Ala Gln

<210> SEQ ID NO 14
<211> LENGTH: 18
<212> TYPE: PRT
<213> ORGANISM: Artificial sequence
<220> FEATURE:
<223> OTHER INFORMATION: synthetic sequence

<400> SEQUENCE: 14

Met Phe Lys Ser Val Val Tyr Ser Ile Leu Ala Ala Ser Leu Ala Asn
1               5                   10                  15

Ala Gly

<210> SEQ ID NO 15
<211> LENGTH: 20
<212> TYPE: PRT
<213> ORGANISM: Artificial sequence
<220> FEATURE:
<223> OTHER INFORMATION: synthetic sequence

<400> SEQUENCE: 15

Met Leu Leu Gln Ala Phe Leu Phe Leu Leu Ala Gly Phe Ala Ala Lys
1               5                   10                  15

Ile Ser Ala Ser
            20

<210> SEQ ID NO 16
<211> LENGTH: 22
<212> TYPE: PRT
<213> ORGANISM: Artificial sequence
<220> FEATURE:
<223> OTHER INFORMATION: synthetic sequence

<400> SEQUENCE: 16

Met Asn Phe Ser Arg Ile Phe Phe Phe Val Phe Ala Cys Leu Thr Ala
1               5                   10                  15

Leu Ala Met Val Asn Ala
            20

<210> SEQ ID NO 17
<211> LENGTH: 19
<212> TYPE: PRT
<213> ORGANISM: Artificial sequence
<220> FEATURE:
<223> OTHER INFORMATION: synthetic sequence
```

-continued

<400> SEQUENCE: 17

Met Arg Ala Phe Leu Ala Leu Ile Phe Leu Thr Phe Val Met Asn Val
1               5                   10                  15

Glu Ser Ser

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

```
<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31
<211> LENGTH: 19
<212> TYPE: PRT
<213> ORGANISM: Artificial sequence
<220> FEATURE:
<223> OTHER INFORMATION: synthetic sequence

<400> SEQUENCE: 31

Gly Gly Gly Gly Ser Gly Gly Gly Ser Gly Ser Thr Gly Gly
1               5                   10                  15

Gly Gly Ser

<210> SEQ ID NO 32
<211> LENGTH: 41
<212> TYPE: PRT
<213> ORGANISM: Artificial sequence
<220> FEATURE:
<223> OTHER INFORMATION: synthetic sequence

<400> SEQUENCE: 32

Gln Thr Ser Ser Pro Ser Arg Glu Ala Ser Val Ser Thr Ser Ser Thr
1               5                   10                  15

Ser Ser Ser Ala Ser Gln Ser Ser Asp Pro Thr Thr Thr Ser Ser Ser
            20                  25                  30

Thr Val Ser Thr Pro Ala Thr Gly Ala
        35                  40

<210> SEQ ID NO 33
<211> LENGTH: 232
<212> TYPE: PRT
<213> ORGANISM: Artificial sequence
<220> FEATURE:
<223> OTHER INFORMATION: synthetic sequence

<400> SEQUENCE: 33

Gln Thr Ser Ser Pro Ser Thr Glu Ala Ser Val Ser Thr Ser Ser Thr
1               5                   10                  15

Ser Ser Ser Ala Ser Gln Ser Ser Asp Pro Thr Thr Thr Ser Ser Ser
            20                  25                  30

Ser Ser Ser Ser Pro Ser Ser Gln Ser Glu Glu Ile Ser Ser Ser
        35                  40                  45

Pro Thr Val Ser Thr Thr Pro Ser Thr Ser Ser Ser Ser Ser Met
    50                  55                  60

Thr Ser Thr Thr Thr Thr Lys Ser Ile Ser Thr Ser Thr Thr Ser Ser
65                  70                  75                  80
```

```
Ala Pro Val Thr Asp Val Thr Val Ser Ser Ser Pro Ser Lys Ser Thr
                85                  90                  95

Ser Thr Ser Thr Ser Thr Glu Thr Ser Lys Thr Pro Thr Ser Met Thr
            100                 105                 110

Glu Tyr Thr Ser Ser Thr Ser Ile Ile Ser Thr Pro Val Ser His Ser
            115                 120                 125

Gln Thr Gly Leu Ser Ala Ser Ser Ser Ser Ser Thr Thr Ser Gly
            130                 135                 140

Ser Ser Ser Thr Lys Ser Glu Ser Ser Thr Thr Ser Gly Ser Ser Gln
145                 150                 155                 160

Ser Val Glu Ser Thr Ser Ser His Ala Thr Val Leu Ala Asn Ser Ala
                165                 170                 175

Glu Met Val Thr Thr Ser Ser Ser Ser Ser Thr Ser Glu Met Ser
                180                 185                 190

Leu Thr Ser Thr Ala Thr Ser Val Pro Val Ser Ser Ser Ser Ser Thr
            195                 200                 205

Thr Tyr Ser Thr Ser Ala Ser Thr Gln Ala Val Thr Thr Thr Ser Ser
            210                 215                 220

Ser Thr Val Ser Thr Thr Ser Ser
225                 230

<210> SEQ ID NO 34
<211> LENGTH: 465
<212> TYPE: PRT
<213> ORGANISM: Artificial sequence
<220> FEATURE:
<223> OTHER INFORMATION: synthetic sequence

<400> SEQUENCE: 34

Gln Thr Ser Ser Pro Ser Thr Glu Ala Ser Val Ser Thr Ser Ser Thr
1               5                   10                  15

Ser Ser Ser Ala Ser Gln Ser Ser Asp Pro Thr Thr Thr Ser Ser Ser
                20                  25                  30

Ser Ser Ser Ser Ser Pro Ser Ser Gln Ser Glu Glu Ile Ser Ser Ser
            35                  40                  45

Pro Thr Val Ser Thr Thr Pro Ser Thr Ser Ser Ser Ser Ser Ser Met
    50                  55                  60

Thr Ser Thr Thr Thr Thr Lys Ser Ile Ser Thr Ser Thr Thr Ser Ser
65                  70                  75                  80

Ala Pro Val Thr Asp Val Thr Val Ser Ser Ser Pro Ser Lys Ser Thr
                85                  90                  95

Ser Thr Ser Thr Ser Thr Glu Thr Ser Lys Thr Pro Thr Ser Met Thr
            100                 105                 110

Glu Tyr Thr Ser Ser Thr Ser Ile Ile Ser Thr Pro Val Ser His Ser
            115                 120                 125

Gln Thr Gly Leu Ser Ala Ser Ser Ser Ser Ser Thr Thr Ser Gly
            130                 135                 140

Ser Ser Ser Thr Lys Ser Glu Ser Ser Thr Thr Ser Gly Ser Ser Gln
145                 150                 155                 160

Ser Val Glu Ser Thr Ser Ser His Ala Thr Val Leu Ala Asn Ser Ala
                165                 170                 175

Glu Met Val Thr Thr Ser Ser Ser Ser Ser Thr Ser Glu Met Ser
                180                 185                 190

Leu Thr Ser Thr Ala Thr Ser Val Pro Val Ser Ser Ser Ser Ser Thr
            195                 200                 205
```

```
Thr Tyr Ser Thr Ser Ala Ser Thr Gln Ala Val Thr Thr Ser Ser
            210                 215                 220

Ser Thr Val Ser Thr Thr Ser Ser Ser Thr Thr Leu Thr Ser Ala Phe
225                 230                 235                 240

Thr His Ser Ser Thr Thr Ser Ser Asp Gln Pro Pro Ser Asp Thr Thr
                245                 250                 255

Ser Pro Ser Thr Thr His Glu Pro His Val Thr Thr Gln Thr Ser Ser
                260                 265                 270

Glu Thr Ser Ser Ser Lys Ser Ser Thr Ser Ser Ser Thr Ser
                275                 280                 285

Gln Thr Ser Glu Ser Ala Thr Pro Ser Asp Ser Val Ser Pro Gly Ser
290                 295                 300

Ser Thr Ser Thr Ser Ser Ser Thr Ser Thr Ser Thr Ser Ile Ser
305                 310                 315                 320

Ser Gly Glu Thr Thr Thr Ser Ser Ser Ser Ala Thr Thr Thr
                325                 330                 335

Ser Asn Ser Ala Thr Leu Ser Val Ser Thr Thr Gln Thr Ser Ile Glu
            340                 345                 350

Ala Ser Ser Ser Thr Thr Ser Thr Ser Ser Ser Thr Ile Thr Thr Ser
                355                 360                 365

Ser Ser Ser Ala His Ile Ser Ser Lys Ser Gln Ser Ser Ile Thr Tyr
370                 375                 380

Pro Ser Ser Ser Thr Ser Ser Ser Thr Ser Ser Ser Ile Ser Ser Glu
385                 390                 395                 400

Ser Glu Ser Phe Glu Ser Thr Ser Ala Glu Asp Ala Pro Ser Thr Ala
                405                 410                 415

Pro Ser Ser Ser Val Ser Ser Lys Ser Ser Thr Ser Thr Thr Ser Ser
                420                 425                 430

Thr Ser Thr Ser Ser Ser Thr Pro Ser Pro Ser Pro Ser Ser Val Ser
            435                 440                 445

Ser Ser Ser Thr Ser Ser Leu Thr Thr Ser Ala Val Ser Thr Pro Ala
        450                 455                 460

Thr
465

<210> SEQ ID NO 35
<211> LENGTH: 649
<212> TYPE: PRT
<213> ORGANISM: Artificial sequence
<220> FEATURE:
<223> OTHER INFORMATION: synthetic sequence

<400> SEQUENCE: 35

Gln Thr Ser Ser Pro Ser Thr Glu Ala Ser Val Ser Thr Ser Ser Thr
1               5                   10                  15

Ser Ser Ser Ala Ser Gln Ser Asp Pro Thr Thr Thr Ser Ser Ser
            20                  25                  30

Ser Ser Ser Ser Pro Ser Ser Gln Ser Glu Glu Ile Ser Ser Ser
            35                  40                  45

Pro Thr Val Ser Thr Thr Pro Ser Thr Ser Ser Ser Ser Ser Met
50                  55                  60

Thr Ser Thr Thr Thr Thr Lys Ser Ile Ser Ser Thr Thr Ser Ser
65                  70                  75                  80

Ala Pro Val Thr Asp Val Thr Val Ser Ser Ser Pro Ser Lys Ser Thr
                85                  90                  95
```

```
Ser Thr Ser Thr Ser Thr Glu Thr Ser Lys Thr Pro Thr Ser Met Thr
            100                 105                 110

Glu Tyr Thr Ser Ser Thr Ser Ile Ile Ser Thr Pro Val Ser His Ser
        115                 120                 125

Gln Thr Gly Leu Ser Ala Ser Ser Ser Ser Ser Thr Thr Ser Gly
    130                 135                 140

Ser Ser Ser Thr Lys Ser Glu Ser Ser Thr Thr Ser Gly Ser Ser Gln
145                 150                 155                 160

Ser Val Glu Ser Thr Ser Ser His Ala Thr Val Leu Ala Asn Ser Ala
                165                 170                 175

Glu Met Val Thr Thr Ser Ser Ser Ser Ser Thr Ser Glu Met Ser
            180                 185                 190

Leu Thr Ser Thr Ala Thr Ser Val Pro Val Ser Ser Ser Ser Thr
        195                 200                 205

Thr Tyr Ser Thr Ser Ala Ser Thr Gln Ala Val Thr Thr Thr Ser Ser
    210                 215                 220

Ser Thr Val Ser Thr Thr Ser Ser Ser Thr Thr Leu Thr Ser Ala Phe
225                 230                 235                 240

Thr His Ser Ser Thr Thr Ser Ser Asp Gln Pro Pro Ser Asp Thr Thr
                245                 250                 255

Ser Pro Ser Thr Thr His Glu Pro His Val Thr Thr Gln Thr Ser Ser
            260                 265                 270

Glu Thr Ser Ser Ser Lys Ser Ser Ser Thr Ser Ser Ser Ser Thr Ser
            275                 280                 285

Gln Thr Ser Glu Ser Ala Thr Pro Ser Asp Ser Val Ser Pro Gly Ser
    290                 295                 300

Ser Thr Ser Thr Ser Ser Ser Ser Thr Ser Thr Ser Thr Ser Ile Ser
305                 310                 315                 320

Ser Gly Glu Thr Thr Thr Ser Ser Ser Ser Ser Ala Thr Thr Thr
            325                 330                 335

Ser Asn Ser Ala Thr Leu Ser Val Ser Thr Thr Gln Thr Ser Ile Glu
                340                 345                 350

Ala Ser Ser Ser Thr Thr Ser Thr Ser Ser Ser Thr Ile Thr Thr Ser
    355                 360                 365

Ser Ser Ser Ala His Ile Ser Ser Lys Ser Gln Ser Ser Ile Thr Tyr
370                 375                 380

Pro Ser Ser Ser Thr Ser Ser Ser Thr Ser Ser Ser Ile Ser Ser Glu
385                 390                 395                 400

Ser Glu Ser Phe Glu Ser Thr Ser Ala Glu Asp Ala Pro Ser Thr Ala
            405                 410                 415

Pro Ser Ser Ser Val Ser Ser Lys Ser Ser Thr Ser Thr Thr Ser Ser
            420                 425                 430

Thr Ser Thr Ser Ser Ser Thr Pro Ser Pro Ser Pro Ser Ser Val Ser
    435                 440                 445

Ser Ser Ser Thr Ser Ser Leu Thr Thr Ser Ala Val Ser Thr Pro Ala
450                 455                 460

Thr Ser His Ser Gln Ser Thr Val Val Thr Thr Thr Thr Ile Thr Thr
465                 470                 475                 480

Ser Thr Gly Pro Val Met Ser Thr Thr Thr Ala Tyr Ser Ser Ser Ser
            485                 490                 495

Thr Ser Ser Ser Glu Ser Ser Glu Val Gln Ser Val Met Ser Ser Thr
            500                 505                 510
```

-continued

Pro Ser Ser Thr Ser Thr Thr Thr Ser Ser Glu Ser Thr Ser Ser Ser
            515                 520                 525

Ser Thr Ala Ser Thr Ser Pro Ser Thr Ser Gln Thr Phe Glu Thr Ser
        530                 535                 540

Pro Thr Ile Gly Gly Val Pro Ser Thr Ser Phe Val Ser Thr Pro
545                 550                 555                 560

Thr Thr Lys Leu Ser His Thr Thr Ser Thr Met Thr Ala Gln Ser Asp
                565                 570                 575

Ser Lys Ser Thr His Ser Ser Ser Thr Ser Thr Glu Asp Lys Ser Ser
            580                 585                 590

Thr Ala Ser Ala Val Asp Glu Ser Thr Thr Thr Ser Thr Ser Thr Glu
        595                 600                 605

Ser Thr Thr Ser Val Thr Ser Gly Thr Ser His Ser Ala Lys Glu Ser
    610                 615                 620

Ser Ser Asn Ser Lys Val Tyr Ser Ser Gln Thr Ala His Ser Ser Ile
625                 630                 635                 640

Ser Val Ala Ser Ser Pro Ser Thr Lys
            645

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 40
<212> TYPE: PRT
<213> ORGANISM: Artificial sequence
<220> FEATURE:
<223> OTHER INFORMATION: synthetic sequence

<400> SEQUENCE: 51

Ile Gln Gln Asn Phe Thr Ser Thr Ser Leu Met Ile Ser Thr Tyr Glu
1               5                   10                  15

Gly Lys Ala Ser Ile Phe Phe Ser Ala Glu Leu Gly Ser Ile Ile Phe
            20                  25                  30

Leu Leu Leu Ser Tyr Leu Leu Phe
        35                  40

<210> SEQ ID NO 52
<211> LENGTH: 40
<212> TYPE: PRT
<213> ORGANISM: Artificial sequence
<220> FEATURE:
<223> OTHER INFORMATION: synthetic sequence

<400> SEQUENCE: 52

Glu Lys Ser Thr Asn Ser Ser Ser Ala Thr Ser Lys Asn Ala Gly
1               5                   10                  15

Ala Ala Met Asp Met Gly Phe Phe Ser Ala Gly Val Gly Ala Ala Ile
            20                  25                  30

Ala Gly Ala Ala Ala Met Leu Leu
        35                  40

<210> SEQ ID NO 53
<211> LENGTH: 43
<212> TYPE: PRT
<213> ORGANISM: Artificial sequence
<220> FEATURE:
<223> OTHER INFORMATION: synthetic sequence

<400> SEQUENCE: 53

Ser Leu Leu Lys Ser Ala Ala Ser Ala Thr Ser Ser Gln Ser Ser
1               5                   10                  15

Ser Lys Ser Lys Gly Ala Ala Gly Ile Ile Glu Ile Pro Leu Ile Phe
            20                  25                  30

Arg Ala Leu Ala Glu Leu Tyr Asn Leu Val Leu
        35                  40

<210> SEQ ID NO 54
<211> LENGTH: 40
<212> TYPE: PRT
<213> ORGANISM: Artificial sequence
<220> FEATURE:
<223> OTHER INFORMATION: synthetic sequence

<400> SEQUENCE: 54

Ser Ser Gly Ala Ser Ser Ser Ser Lys Ser Lys Gly Asn Ala
1               5                   10                  15

Ala Ile Met Ala Pro Ile Gly Gln Thr Thr Pro Leu Val Gly Leu Leu
            20                  25                  30

Thr Ala Ile Ile Met Ser Ile Met
        35                  40

<210> SEQ ID NO 55
<211> LENGTH: 44
<212> TYPE: PRT
<213> ORGANISM: Artificial sequence
<220> FEATURE:
<223> OTHER INFORMATION: synthetic sequence

<400> SEQUENCE: 55

Ala Gln Ala Asn Val Ser Ala Ser Ala Ser Ser Ser Ser Ser Ser
1               5                   10                  15

Lys Lys Ser Lys Gly Ala Ala Pro Glu Leu Val Pro Ala Thr Ser Phe
            20                  25                  30

Met Gly Val Val Ala Ala Val Gly Val Ala Leu Leu
        35                  40

<210> SEQ ID NO 56
<211> LENGTH: 40
<212> TYPE: PRT
<213> ORGANISM: Artificial sequence
<220> FEATURE:
<223> OTHER INFORMATION: synthetic sequence

```
<400> SEQUENCE: 56

Gly Pro Gly Glu Lys Ala Arg Lys Asn Asn Ala Ala Pro Gly Pro Ser
1               5                   10                  15

Asn Phe Asn Ser Ile Lys Leu Phe Gly Val Thr Ala Gly Ser Ala Ala
            20                  25                  30

Val Ala Gly Ala Leu Leu Leu Leu
            35                  40

<210> SEQ ID NO 57
<211> LENGTH: 39
<212> TYPE: PRT
<213> ORGANISM: Artificial sequence
<220> FEATURE:
<223> OTHER INFORMATION: synthetic sequence

<400> SEQUENCE: 57

Ser Ser Thr Gly Met Leu Ser Pro Thr Ser Ser Ser Thr Arg Lys
1               5                   10                  15

Glu Asn Gly Gly His Asn Leu Asn Pro Pro Phe Phe Ala Arg Phe Ile
            20                  25                  30

Thr Ala Ile Phe His His Ile
            35

<210> SEQ ID NO 58
<211> LENGTH: 40
<212> TYPE: PRT
<213> ORGANISM: Artificial sequence
<220> FEATURE:
<223> OTHER INFORMATION: synthetic sequence

<400> SEQUENCE: 58

Ser Ser Phe Ser Ser Ser Gly Gly Ser Ser Glu Ser Thr Thr Lys Lys
1               5                   10                  15

Gln Asn Ala Gly Tyr Lys Tyr Arg Ser Ser Phe Ser Phe Ser Leu Leu
            20                  25                  30

Ser Phe Ile Ser Tyr Phe Leu Leu
            35                  40

<210> SEQ ID NO 59
<211> LENGTH: 40
<212> TYPE: PRT
<213> ORGANISM: Artificial sequence
<220> FEATURE:
<223> OTHER INFORMATION: synthetic sequence

<400> SEQUENCE: 59

Tyr Lys Ser Thr Val Asn Gly Lys Val Ala Ser Val Met Ser Asn Ser
1               5                   10                  15

Thr Asn Gly Ala Thr Ala Gly Thr His Ile Ala Tyr Gly Ala Gly Ala
            20                  25                  30

Phe Ala Val Gly Ala Leu Leu Leu
            35                  40

<210> SEQ ID NO 60
<211> LENGTH: 40
<212> TYPE: PRT
<213> ORGANISM: Artificial sequence
<220> FEATURE:
<223> OTHER INFORMATION: synthetic sequence
```

```
<400> SEQUENCE: 60

Ser Gly Asn Leu Thr Thr Ser Thr Ala Ser Ala Thr Ser Thr Ser Ser
1               5                   10                  15

Lys Arg Asn Val Gly Asp His Ile Val Pro Ser Leu Pro Leu Thr Leu
                20                  25                  30

Ile Ser Leu Leu Phe Ala Phe Ile
            35                  40

<210> SEQ ID NO 61
<211> LENGTH: 43
<212> TYPE: PRT
<213> ORGANISM: Artificial sequence
<220> FEATURE:
<223> OTHER INFORMATION: synthetic sequence

<400> SEQUENCE: 61

Gly Lys Asn Gly Ala Lys Ser Gln Gly Ser Ser Lys Lys Met Glu Asn
1               5                   10                  15

Ser Ala Pro Lys Asn Ile Phe Ile Asp Ala Phe Lys Met Ser Val Tyr
                20                  25                  30

Ala Val Phe Thr Val Leu Phe Ser Ile Ile Phe
            35                  40

<210> SEQ ID NO 62
<211> LENGTH: 40
<212> TYPE: PRT
<213> ORGANISM: Artificial sequence
<220> FEATURE:
<223> OTHER INFORMATION: synthetic sequence

<400> SEQUENCE: 62

Thr Gly Ser Ser Ser Ala Ser Ser Ser Lys Ser Lys Gly Val Gly
1               5                   10                  15

Asn Ile Val Asn Val Ser Phe Ser Gln Ser Gly Tyr Leu Ala Leu Phe
                20                  25                  30

Ala Gly Leu Ile Ser Ala Leu Leu
            35                  40

<210> SEQ ID NO 63
<211> LENGTH: 40
<212> TYPE: PRT
<213> ORGANISM: Artificial sequence
<220> FEATURE:
<223> OTHER INFORMATION: synthetic sequence

<400> SEQUENCE: 63

Ala Ser Gly Ser Ser Thr His Lys Lys Asn Ala Gly Asn Ala Leu Val
1               5                   10                  15

Asn Tyr Ser Asn Leu Asn Thr Asn Thr Phe Ile Gly Val Leu Ser Val
                20                  25                  30

Ile Ser Ala Val Phe Gly Leu Ile
            35                  40

<210> SEQ ID NO 64
<211> LENGTH: 40
<212> TYPE: PRT
<213> ORGANISM: Artificial sequence
<220> FEATURE:
<223> OTHER INFORMATION: synthetic sequence
```

-continued

```
<400> SEQUENCE: 64

Glu Asp Ala Asp Glu Asp Lys Asp Asp Leu Lys Arg Lys His Arg Asn
1               5                   10                  15

Ser Ala Ser Ile Ser Gly Pro Leu Leu Pro Leu Gly Leu Cys Leu Leu
            20                  25                  30

Phe Phe Thr Phe Ser Leu Phe Phe
            35                  40

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
<211> LENGTH: 37
<212> TYPE: PRT
<213> ORGANISM: Artificial sequence
<220> FEATURE:
<223> OTHER INFORMATION: synthetic sequence

<400> SEQUENCE: 71

Gln Ile Gln Ser Ser Met Val Glu Ile Ser Thr Tyr Ala Gly Ser Ala
1               5                   10                  15

Asn Ser Val Asn Ala Gly Ala Gly Ala Gly Ala Leu Phe Leu Leu Leu
            20                  25                  30

Ser Leu Ala Ile Ile
            35
```